United States Patent [19]

Rubsamen et al.

[11] Patent Number: 5,672,581
[45] Date of Patent: *Sep. 30, 1997

[54] METHOD OF ADMINISTRATION OF INSULIN

[75] Inventors: Reid M. Rubsamen, Berkeley; Lester John Lloyd, Orinda, both of Calif.

[73] Assignee: Aradigm Corporation, Hayward, Calif.

[*] Notice: The term of this patent shall not extend beyond the expiration date of Pat. No. 5,364,838.

[21] Appl. No.: 331,056

[22] Filed: Oct. 28, 1994

Related U.S. Application Data

[63] Continuation-in-part of Ser. No. 11,281, Jan. 29, 1993, Pat. No. 5,364,838.

[51] Int. Cl.$^6$ .................. A61K 38/26; A61K 38/02; C07K 5/00; C07K 7/00
[52] U.S. Cl. .................. 514/3; 514/4; 530/303; 424/489; 424/43
[58] Field of Search .................. 514/2, 3, 4; 424/489, 424/43, 145; 435/4, 810; 530/303; 128/200.14, 200.16, 200.23, 200.24, 203.12, 203.15

[56] References Cited

U.S. PATENT DOCUMENTS

| | | | |
|---|---|---|---|
| 3,812,854 | 5/1974 | Michaels et al. | 128/194 |
| 3,991,304 | 11/1976 | Hillsman | 235/151.34 |
| 4,106,503 | 8/1978 | Rosenthal et al. | 128/194 |
| 4,361,401 | 11/1982 | Smith et al. | |
| 4,604,847 | 8/1986 | Moulding, Jr. et al. | 53/75 |
| 4,627,432 | 12/1986 | Newell et al. | |
| 4,677,975 | 7/1987 | Edgar et al. | 128/200.14 |
| 4,686,231 | 8/1987 | Bender et al. | 514/333 |
| 4,819,629 | 4/1989 | Jonson et al. | 128/203.32 |
| 4,877,989 | 10/1989 | Drews et al. | |
| 4,926,852 | 5/1990 | Zoltan et al. | |
| 4,984,158 | 1/1991 | Hillsman | 364/413.04 |
| 5,011,678 | 4/1991 | Wang et al. | 424/45 |
| 5,167,506 | 12/1992 | Kilis et al. | 434/262 |
| 5,364,838 | 11/1994 | Rubsamen | 514/3 |
| 5,497,944 | 3/1996 | Weston et al. | 239/321 |

FOREIGN PATENT DOCUMENTS

| | | | |
|---|---|---|---|
| 0 186 280 | 10/1985 | European Pat. Off. | A61M 13/00 |
| 0 232 235 A2 | 8/1987 | European Pat. Off. | A61M 15/00 |
| 2 104 393 | 3/1983 | United Kingdom | A61M 11/00 |
| 2 153 0 81 | 8/1985 | United Kingdom | A61M 5/14 |
| 2 255 918 | 11/1992 | United Kingdom | |
| 2 256 805 | 12/1992 | United Kingdom | A61M 11/00 |
| WO 91/14468 | 10/1991 | WIPO | A61M 11/00 |
| 91/01868 | 5/1992 | WIPO | A61M 15/00 |
| WO 92/09322 | 6/1992 | WIPO | A61M 15/00 |
| 92/01815 | 9/1992 | WIPO | A61M 11/00 |
| WO 93/17728 | 9/1993 | WIPO | A61M 15/00 |

OTHER PUBLICATIONS

Colthorpe, P. et al., "The pharmacokinetics of Pulmonary--Delivered Insulin: A comparison of intratracheal and aerosol administration to the rabbit", 1992, Pharmaceutical Research, 9:764–768.

Elliott, R.B. et al., "Parenteral absorption of insulin from the lung in diabetic children", 1987, Aust. Paediatr. J. 23:293–297.

Kohler, D., "Aerosols for Systemic Treatment", 1990, Lung, Suppl.:677–684.

Lauber, B.L. et al., "Deposition, Clearance, and Effects in the Lung", Journal of Aerosol Medicine, 4:286.

Lauber, B.L. et al., "Preliminary Study of the Efficacy of insulin aerosol delivered by oral inhalation in diabetic patients," 1994, JAMA, 269:2106–2109.

Moses, A.C. et al., "Insulin administered intranasally as an insulin–bile salt aerosol–Effectiveness and Reproducibility in Normal and Diabetic Subjects", 1983, Diabetes, 32:1040–1047.

Newman, S.P. et al., "Deposition of pressurized aerosols in the human respiratory tract", 1981, Thorax, 36:52–55.

Newman, S.P. et al., "How should a pressurized β–adrenergic bronchodilator be inhaled?", 1981, Eur. J. Respir. Dis. 62:3–21.

Newman, S.P. et al., "Deposition of pressurized suspension aerosols inhaled through extension devices", 1981, Am. Rev. Respir. Dis. 124:317–320.

Newman, S.P., "Deposition and Effects of Inhalation Aerosols", 1983.

Remington's Pharmaceutical Sciences, A.R. Gennaro, ed., 1985, Mack Publishing Co.

Salzman, R., "Intranasal aerosolized insulin mixed–meal studies and long–term use in type 1 diabetes", 1985, New England Journal of Medicine, 213:1078–1084.

Wigley, F.M. et al., "Insulin across respiratory mucosae by aerosol delivery", 1971, Diabetes, 20:552–556.

Yoshida, H. et al., "Absorption of insulin delivered to rabbit trachea using aerosol dosage form", 1979, J. Pharmaceutical Sciences 68:670–671.

*Primary Examiner*—Avis M. Davenport
*Attorney, Agent, or Firm*—Karl Bozicevic; Fish & Richardson P.C.

[57] ABSTRACT

A method for treating a patient suffering from diabetes mellitus by delivering aerosolized insulin to the patient and a programmed, portable, hand-held device used in such treatment methodology is disclosed. Two basic types of drug delivery devices are disclosed for use in connection with the present invention. In accordance with the first type of device the insulin is contained within a low boiling point propellant which is held within a canister under pressure. In accordance with the second type of device the insulin is present within a container in solution and the solution is moved through a porous membrane to create an aerosolized formulation which is inhaled by the patient. In accordance with both devices a measured amount of insulin containing formulation is automatically released into the inspiratory flow path of a patient in response to information obtained from determining the inspiratory flow rate and inspiratory volume of a patient. The determination of values and release of drugs are carried out in real time. Reproducibly dosing of insulin to the patient is obtained by repeatedly providing for automatic release of insulin formulation at the same inspiratory flow rate and inspiratory volume. To maximize the efficiency of the delivery of the insulin formulation the formulation is released at an inspiratory flow rate in the range of from about 0.1 to about 2.0 liters/second and a measured inspiratory volume in the range of about 0.1 to about 0.8 liters.

20 Claims, 10 Drawing Sheets

METHOD OF ADMINISTRATION OF INSULIN

CROSS REFERENCE TO RELATED APPLICATIONS

This application is a continuation-in-part of earlier filed application Ser. No. 08/011,281 filed Jan. 29, 1993 now U.S. Pat. No. 5,364,838 which application is incorporated herein by reference and to which application is claimed priority under 35 USC §120.

FIELD OF THE INVENTION

This invention relates generally to methods of treating humans suffering from diabetes mellitus. More specifically, this invention relates to the controlled intrapulmonary delivery of insulin alone or in combination with other treatment methodologies which are combined to significantly reduce or eliminate the need for administering insulin by injection.

BACKGROUND OF THE INVENTION

Diabetes Mellitus is a disease affecting approximately 7.5 million persons in the United States. The underlying cause of this disease is diminished or absent insulin production by the Islets of Langerhans in the pancreas. Of the 7.5 million diagnosed diabetics in the United States, approximately one-third are treated using insulin replacement therapy. Those patients receiving insulin typically self-administer one or more doses of the drug per day by subcutaneous injection.

Insulin is a polypeptide with a nominal molecular weight of 6,000 Daltons. Insulin has traditionally been produced by processing pig and cow pancreas to allow isolation of the natural product. More recently, recombinant technology has made it possible to produce human insulin in vitro. It is the currently common practice in the United States to institute the use of recombinant human insulin in all of those patients beginning insulin therapy.

It is known that most proteins are rapidly degraded in the acidic environment of the GI tract. Since insulin is a protein which is readily degraded in the GI tract, those in need of the administration of insulin administer the drug by subcutaneous injection (SC). No satisfactory method of orally administering insulin has been developed. The lack of such an oral delivery formulation for insulin creates a problem in that the administration of drugs by injection can be both psychologically and physically painful.

In an effort to provide for a non-invasive means for administering insulin, and thereby eliminate the need for hypodermic syringes, aerosolized insulin formulations have been theorized. Aerosolized insulin formulations have been shown to produce insulin blood levels in man when these aerosols are introduced onto nasal or pulmonary membrane. Moses et al. [*Diabetes*, Vol. 32, November 1983] demonstrated that a hypoglycemic response could be produced following nasal administration of 0.5 units/kg. Significant inter-subject variability was noted, and the nasal insulin formulation included unconjugated bile salts to promote nasal membrane penetration of the drug. Salzman et al. [*New England Journal of Medicine*, Vol. 312, No. 17] demonstrated that an intranasal aerosolized insulin formulation containing a non-ionic detergent membrane penetration enhancer was effective in producing a hypoglycemic response in diabetic volunteers. Their work demonstrated that nasal irritation was present in varying degrees among the patients studied. In that diabetes is a chronic disease which must be continuously treated by the administration of insulin and in that mucosal irritation tends to increase with repeated exposures to the membrane penetration enhancers, efforts at developing a non-invasive means of administering insulin via nasal administration have not been commercialized.

In 1971, Wigley et al. [*Diabetes*, Vol 20, No. 8] demonstrated that a hypoglycemic response could be observed in patients inhaling an aqueous formulation of insulin into the lung. Radio-immuno assay techniques demonstrated that approximately 10 percent of the inhaled insulin was recovered in the blood of the subjects. Because the surface area of membranes available to absorb insulin is much greater in the lung than in the nose, no membrane penetration enhancers are required for delivery of insulin to the lungs by inhalation. The inefficiency of delivery seen by Wigley was greatly improved in 1979 by Yoshida et al. [*Journal of Pharmaceutical Sciences*, Vol. 68, No. 5] who showed that almost 40 percent of insulin delivered directly into the trachea of rabbits was absorbed into the bloodstream via the respiratory tract. Both Wigley and Yoshida showed that insulin delivered by inhalation could be seen in the bloodstream for two or more hours following inhalation.

Aerosolized insulin therefore can be effectively given if the aerosol is appropriately delivered into the lung. In a review article, Dieter Kohler [*Lung*, supplement pp. 677–684] remarked in 1990 that multiple studies have shown that aerosolized insulin can be delivered into the lung with an expected half-life of 15–25 minutes. However, he comments that "the poor reproducibility of the inhaled dose [of insulin] was always the reason for terminating these experiments." This is an important point in that the lack of precise reproducibility with respect to the administration of insulin is critical. The problems associated with the insufficient administration of insulin cannot be compensated for by administering excess amounts of the drug in that the administration of too much insulin can be fatal.

Effective use of an appropriate nebulizer can achieve high efficiency in delivering insulin to human subjects. Laube et al. [*Journal of Aerosol Medicine*, Vol. 4, No. 3, 1991] have shown that aerosolized insulin delivered from a jet nebulizer with a mass median aerodynamic diameter of 1.12 microns, inhaled via a holding chamber at a slow inspiratory flow rate of 17 liters/minute, produced an effective hypoglycemic response in test subjects at a dose of 0.2 units/kg. Colthorpe et al. [*Pharmaceutical Research*, Vol. 9, No. 6, 1992] have shown that aerosolized insulin given peripherally into the lung of rabbits produces a bioavailability of over 50.7 percent in contrast to 5.6 percent bioavailability seen for liquid insulin dripped onto the central airways. Colthorpe's work supports the contention that aerosolized insulin must be delivered peripherally into the lung for maximum efficiency and that inadvertent central deposition of inhaled aerosolized insulin will produce an effect ten times lower than that desired. Variations in dosing of 10-fold are clearly unacceptable with respect to the administration of most drugs, and in particular, with respect to the administration of insulin.

The present invention endeavors to overcome the problems of the prior art by eliminating the need for permeation enhancers and thus eliminating mucosal irritation and providing a non-invasive methodology for repeatedly providing a controlled dosage amount of insulin to a patient.

SUMMARY OF THE INVENTION

A method for treating a patient suffering from diabetes mellitus by delivering aerosolized insulin to the patient and a programmed, portable, hand-held device used in such treatment methodology is disclosed. Two basic types of drug delivery devices are disclosed for use in connection with the present invention. In accordance with the first type of device the insulin is contained within a low boiling point propellant which is held within a canister under pressure. In accordance with the second type of device the insulin is present within a container in a dry state which container is interconnected to another container which holds a solvent for the insulin such as water or ethanol. Prior to use the solvent is brought into contact with the insulin to dissolve the insulin. Thereafter, the solution is moved through a porous membrane to create an aerosolized formulation which is inhaled by the patient. In accordance with both devices a measured amount of insulin containing formulation is automatically released into the inspiratory flow path of a patient in response to information obtained from a means for measuring and separately determining inspiratory flow rate and inspiratory volume of a patient. Reproducible dosing of insulin to the patient is obtained by providing for automatic release of insulin formulation in response to a determined inspiratory flow rate and measured inspiratory volume. The method involves measuring for, determining and/or calculating a firing point or drug release decision based on instantaneously (or real time) calculated, measured and/or determined inspiratory flow rate and inspiratory volume points. To obtain repeatability in dosing the insulin formulation is repeatedly released at the same measured (1) inspiratory flow rate and (2) inspiratory volume. To maximize the efficiency of the delivery of the insulin formulation the formulation is released at (3) a measured inspiratory flow rate in the range of from about 0.1 to about 2.0 liters/second and (2) a measured inspiratory volume in the range of about 0.1 to about 0.8 liters.

A primary object of the invention is to provide for a non-invasive means of treating diabetes mellitus.

Another object is to provide a method of administering insulin to a patient wherein aerosolized insulin formulation is repeatedly delivered to a patient at the same measured inspiratory flow rate (in the range of 0.1 to 2.0 liters/second) and separately determined inspiratory volume (in the range of 0.15 to 0.8 liters).

Another object is to provide an insulin-containing package which package may include one or more containers of insulin in a dry powdered form and, in addition one or more containers of a solvent for the insulin the containers being positioned such that the solvent can be brought into contact with and dissolve the insulin prior to being moved through a porous membrane of the insulin-containing container.

Another object of the invention is to provide a device which allows for the intrapulmonary delivery of controlled amounts of insulin based on the particular needs of the diabetic patient including serum glucose levels and insulin sensitivity.

Another object of the invention is to provide a means for treating diabetes mellitus which involves supplementing insulin administration using an intrapulmonary delivery means in combination with injections of insulin and/or oral hypoglycemic agents such as sulfonylureas.

Another object of the invention is to combine insulin delivery therapies with monitoring technologies so as to maintain tight control over the serum glucose level of a patient suffering from diabetes mellitus.

Yet another object of the invention is to provide methods of treating diabetics using the intrapulmonary delivery of all types of insulin formulations including rapid, intermediate and long-acting preparations.

Another advantage of the present invention is that the methodology allows the administration of smaller doses of insulin by a convenient and painless route, thus decreasing the probability of insulin overdosing and increasing the probability of safely maintaining desired serum glucose levels.

Another advantage of the present invention is that the device can be readily used in public without the disturbing effects associated with publicly administering a drug by injection.

A feature of the present invention is that the device can be programmed for the particular needs of individual patients.

Another feature of the device of the present invention is that it may be programmed to provide variable dosing so that different doses are delivered to the patient at different times of the day coordinated with meals and/or other factors important to maintain proper serum glucose levels with the particular patient.

Another feature of the invention is that the portable, hand-held inhalation device of the invention can be used in combination with a portable device for measuring serum glucose levels in order to closely monitor and titrate dosing based on actual glucose levels.

Yet another feature of the invention is that the microprocessor of the delivery device can be programmed to prevent overdosing by preventing the valve from being opened more than a given number of times within a given period of time.

These and other objects, advantages and features of the present invention will become apparent to those persons skilled in the art upon reading the details of the structure of the device, formulation of compositions and methods of use, as more fully set forth below.

DETAILED DESCRIPTION OF PREFERRED EMBODIMENTS

Figure 1:
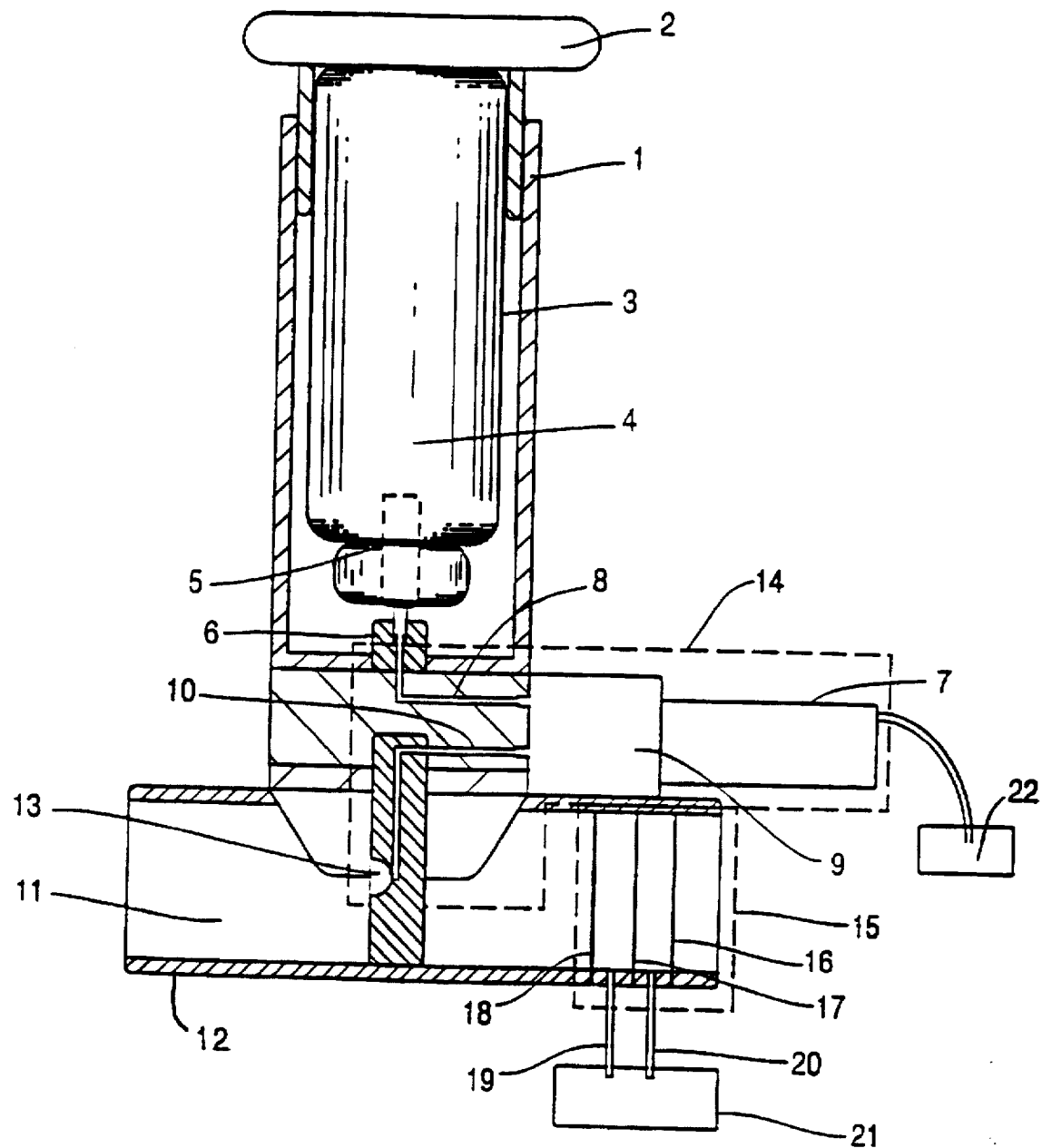
FIG. 1 is a cross-sectional view of an embodiment of an aerosolizing drug delivery device.

Before the present method of delivery aerosolized insulin and treating diabetes mellitus and devices and formulations used in connection with such are described, it is to be understood that this invention is not limited to the particular methodology, devices and formulations described, as such methods, devices and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "and," and "the" include plural referents unless the context clearly dictates otherwise. Thus, for example, reference to "a formulation" includes mixtures of different formulations, reference to "an analog" refers to one or mixtures of insulin analogs, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods, devices and materials similar or equivalent to those described herein can be used in the practice or testing of the invention, the preferred methods, devices and materials are now described. All publications mentioned herein are incorporated herein by reference for the purpose of describing and disclosing devices, formulations and methodologies which are described in the publication and which might be used in connection with the presently described invention.

Definitions

The term "insulin" shall be interpreted to encompass natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form which includes additional excipients. The insulin is preferably recombinantly produced and may be dehydrated (completely dried) or in solution.

The term "insulin analog" is intended to encompass any form of "insulin" as defined above wherein one or more of the amino acids within the polypeptide chain has been replaced with an alternative amino acid and/or wherein one or more of the amino acids has been deleted or wherein one or more additional amino acids has been added to the polypeptide chain. In general, the "insulin analogs" of the present invention include "super insulin analogs" wherein the ability of the insulin analog to affect serum glucose levels is substantially enhanced as compared with conventional insulin as well as hepatoselective insulin analogs which are more active in the liver than in adipose tissue.

The term "acceptable serum glucose level" is intended to mean a glucose level above 50 mg/dl and below 300 mg/dl more preferably 80 mg/dl to 200 mg/dl and most preferably about 100 mg/dl. It will be understood by those skilled in the art that levels of about 50 mg/dl are considered low and that levels of about 300 mg/dl are considered high, although acceptable in the sense that these levels are generally not fatal. It is an important aspect of the invention to maintain more acceptable levels which are above the low of 50 mg/dl and below the high of 300 mg/dl with it being more acceptable to deliver doses of insulin so as to keep the patient as close as possible to about 100 mg/dl.

The term "velocity of the drug" or "aerosol velocity" shall mean average speed of particles moving from a drug release point such a valve or membrane to a patient's mouth.

The term "dosing event" shall be interpreted to mean the administration of insulin and/or an insulin analog to a patient in need thereof by the intrapulmonary route of administration which event may encompass one or more releases of insulin formulation from an insulin dispensing device over a period of time of 15 minutes or less, preferably 10 minutes or less, and more preferably 5 minutes or less, during which period multiple inhalations are made by the patient and multiple doses of insulin are released and inhaled. A dosing event shall involve the administration of insulin to the patient in an amount of about 1 unit to about 30 units in a single dosing event which may involve the release of from about 10 to about 300 units of insulin from the device.

The term "measuring" describes an event whereby either or both the inspiratory flow rate and inspiratory volume of the patient is measured in order to determine an optimal point in the inspiratory cycle at which to release aerosolized insulin formulation. It is also preferable to continue measuring inspiratory flow during and after any drug delivery and to record inspiratory flow rate and volume before, during and after the release of drug. Such reading makes it possible to determine if insulin formulation was properly delivered to the patient. A microprocessor or other device can calculate volume based on a measured flow rate. When either flow rate or volume becomes known in any manner it can be said to have been determined.

The term "monitoring" event shall mean measuring lung functions such as inspiratory flow, inspiratory flow rate, and/or inspiratory volume so that a patient's lung function as defined herein, can be evaluated before and/or after drug delivery thereby making it possible to evaluate the effect, if any, of insulin delivery on the patient's lung function.

The term "inspiratory flow rate" shall mean a value of air flow rate measured, calculated and/or determined based on the speed of the air passing a given point in a measuring device assuming atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data and assuming atmospheric pressure, ±5% and temperature in the range of about 10° C. to about 40° C.

The term "inspiratory volume" shall mean a determined, calculated and/or measured volume of air passing a given point into the lungs of a patient assuming atmospheric pressure ±5% and a temperature in the range of 10° C. to 40° C.

The term "inspiratory flow profile" shall be interpreted to mean data calculated in one or more events measuring inspiratory flow and cumulative volume, which profile can be used to determine a point within a patient's inspiratory cycle which is preferred for the release of drug to be delivered to a patient. The point within the inspiratory cycle where drug is released may be based on a point within the inspiratory cycle likely to result in the maximum delivery of drug and based and/or on a point in the cycle most likely to result in the delivery of a reproducible amount of drug to the patient at each release of drug. Repeatability of the amount delivered is the primary criterion and maximizing the amount delivered is an important but secondary criterion. Thus, a large number of different drug release points might be selected and provide for repeatability in dosing provided the selected point is again selected for subsequent releases. To insure maximum drug delivery the point is selected within given parameters.

The term "therapeutic index" refers to the therapeutic index of a drug defined as $LD_{50}/ED_{50}$. The $LD_{50}$ (lethal dose, 50%) is defined as the dose of a drug which kills 50% of the tested animals, and the $ED_{50}$ is defined as the effective dose of the drug for 50% of the individuals treated. Drugs with a therapeutic index near unity (i.e. $LD_{50}/ED_{50}$ is approximately equal to 1) achieve their therapeutic effect at doses very close to the toxic level and as such have a narrow therapeutic window, i.e. a narrow dose range over which they may be administered.

The terms "formulation" and "liquid formulation" and the like are used interchangeably herein to describe any pharmaceutically active insulin, analog thereof, or other drug for treating diabetes mellitus by itself or with a pharmaceutically acceptable carrier in flowable liquid form. Such formulations are preferably solutions, e.g. aqueous solutions, ethanolic solutions, aqueous/ethanolic solutions, saline solutions and colloidal suspensions. Formulations can be solutions or suspensions of drug in a low boiling point propellant.

The terms "lung function" and "pulmonary function" are used interchangeably and shall be interpreted to mean physically measurable operations of a lung including but not limited to (1) inspiratory and (2) expiratory flow rates as well as (3) lung volume. Methods of quantitatively determining pulmonary function are used to measure lung function. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of such events may be carried out and repeated over time.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

General Methodology

The essence of the invention is to provide a non-invasive means of treating diabetes mellitus in a manner which makes it possible to accurately dose the administration of aerosolized insulin and thereby maintain tight control over serum glucose levels of a patient suffering from the disease. An essential feature of the invention is the intrapulmonary delivery of insulin to the patient in a controlled and repeatable manner with or without any monitoring of glucose levels. The device of the invention provides a number of features which make it possible to achieve the controlled and repeatable dosing procedure required for treating diabetes.

Specifically, the device is not directly actuated by the patient in the sense that no button is pushed nor valve released by the patient applying physical pressure. On the contrary, the device of the invention provides that aerosolized insulin formulation is released automatically upon receipt of a signal from a microprocessor programmed to send a signal when data is received from a monitoring device such as an airflow rate monitoring device.

A patient using the device withdraws air from a mouthpiece and the inspiratory rate of the patient is measured as is cumulative respiratory volume one or more times in a monitoring event which determines an preferred point in an inhalation cycle for the release of a dose of insulin. Inspiratory flow is measured and recorded in one or more monitoring events for a given patient in order to develop an inspiratory flow profile for the patient. The recorded information is analyzed by the microprocessor in order to deduce a preferred point within the patient's respiratory cycle for the release of insulin with the preferred point being calculated based on the most likely point to result in a reproducible delivery event. The monitoring device continually sends information to the microprocessor, and when the microprocessor determines that the optimal point in the respiratory cycle is reached, the microprocessor actuates the opening of the valve allowing release of insulin. Accordingly, drug is always delivered at a pre-programmed place in the respiratory flow profile of the particular patient which is selected specifically to maximize reproducibility of drug delivery and peripheral dispersion of the drug. It is pointed out that the device of the present invention can be used to, and actually does, improve the efficiency of drug delivery. However, this is not the critical feature. The critical feature is the reproducibility of the release of a tightly controlled amount of drug at a particular point in the inspiratory cycle so as to assure the delivery of a controlled and repeatable amount of drug to the lungs of each individual patient.

The combination of automatic control of the valve release, combined with frequent monitoring events in order to calculate the optimal flow rate and time for the release of insulin, combine to provide a repeatable means of delivering insulin to a patient. Because the valve is released automatically and not manually, it can be predictably and repeatedly opened for the same amount of time each time or for the preprogrammed measured amount of time which is desired at that particular dosing event. Because dosing events are preferably preceded by monitoring events, the amount of insulin released and/or the point in the inspiratory cycle of the release can be readjusted based on the particular condition of the patient. For example, if the patient's total volume should change, such will be taken into account in the monitoring event by the microprocessor which will readjust the amount and/or point of release of the insulin in a manner calculated to provide for the administration of the same amount of insulin to the patient at each dosing event.

There is considerable variability with respect to the amount of insulin which is delivered to a patient when the insulin is being administered by injection. Patients requiring the administration of injectable insulin use commercial insulin which is prepared in concentrations of 100 units per milliliter, although higher concentrations up to about 500 units per milliliter can be obtained. It is preferable to use the more highly concentrated insulin in connection with the present invention. If insulin containing 500 units of insulin per milliliter is used and a patient is administering 5 units, then the patient will only need to administer 0.01 milliliters of the concentrated insulin to the lungs of the patient to achieve the desired dose.

The symptoms of diabetes can be readily controlled with the administration of insulin. However, it is extremely difficult, and probably impossible, to normalize the blood sugar throughout a 24-hour period utilizing traditional insulin therapy given as one or two injections per day. It is possible to more closely approach normalized blood sugar levels with the present invention. Improvements are obtained by smaller, more frequent dosing and by timing dosing relative to meals, exercise and sleep.

The precise amount of insulin administered to a patient varies considerably depending upon the degree of the disease and the size of the patient. A normal-weight adult may be started on about a 15-20 units a day in that the estimated daily insulin production rate in non-diabetic subjects of normal size is approximately 25 units per day. It is preferable to administer approximately the same quantity of insulin for several days before changing the dosing regime except with hypoglycemic patients for which the dose should be immediately decreased unless a clearly evident nonrecurrent cause of hypoglycemia (such as not eating, i.e., missing a typical meal) is present. In general, the changes should not be more than five to ten units per day. It is typical to administer about two-thirds of the total insulin daily dosage before breakfast and administer the remainder before supper. When the total dosage reaches 50 or 60 units per day, a plurality of smaller doses are often required since peak action of insulin appears to be dose related, i.e., a low dose may exhibit maximal activity earlier and disappear sooner than a large dose. All patients are generally instructed to reduce insulin dosage by about 5 to 10 units per day when extra activity is anticipated. In a similar manner, a small amount of extra insulin may be taken before a meal that contains extra calories or food which is not generally eaten by the diabetic patient. The inhalation device of the present invention is particularly useful with respect to providing such small amounts of additional insulin.

Several types of insulin formulations are commercially available. When larger doses of insulin must be administered at a single point in time, it may be preferable to administer intermediate or long-acting insulin formulations. Such formulations release some insulin immediately and provide a more sustained release of the remainder of the insulin over time. Such formulations are described further below in the "Insulin Containing Formulations" section.

When administering insulin using the inhalation device of the present invention, the entire dosing event can involve the administration of anywhere from one to 25 units, but more preferably involves the administration of approximately five to ten units. The entire dosing event may involve several inhalations by the patient with each of the inhalations being provided with multiple bursts of insulin from the device. For example, the device can be programmed so as to release enough insulin so that approximately one unit of insulin is delivered to the patient per inhalation or 0.33 units of insulin per burst with three bursts being delivered per inhalation. If ten units are to be delivered, the ten units are delivered by releasing 33 bursts in ten different inhalations. Such a dosing event should take about 1–2 minutes to deliver 10 units of insulin. Since only small amounts are delivered with each burst and with each inhalation, even a complete failure to deliver insulin with a given inhalation or burst is not of great significance and will not seriously disturb the reproducibility of the dosing event. Further, since relatively small amounts are delivered with each inhalation and/or burst, the patient can safely administer an additional unit or two of insulin without fear of overdosing.

There is a differential between the amount of insulin actually released from the device and the amount of insulin actually delivered to the patient. In general, the present device is approximately 20% efficient, however, the efficiency can be as low as 10% and as high as 50% or more meaning that as little as 10% of the released insulin may actually reach the circulatory system of the patient and as much as 50% or more might be delivered. The efficiency of the delivery will vary somewhat from patient to patient and must be taken into account when programming the device for the release of insulin. In general, a conventional metered dose inhaling device is about 10% efficient.

Obese patients are generally somewhat less sensitive to insulin and must be provided with higher doses of insulin in order to achieve the same effect as normal weight patients. Dosing characteristics based on insulin sensitivity are known to those skilled in the art and are taken into consideration with respect to the administration of injectable insulin. The present invention makes it possible to vary dosing over time if insulin sensitivity changes and/or if user compliance and/or lung efficiency changes over time.

Based on the above, it will be understood that the dosing or amount of insulin actually released from the device can be changed based on the most immediately prior monitoring event wherein the inspiratory flow of a patient's inhalation is measured. The amount of insulin released can also be varied based on factors such as timing and timing is, in general, connected to meal times, sleep times and, to a certain extent, exercise times. Although all or any of these events can be used to change the amount of insulin released from the device and thus the amount of insulin delivered to the patient, ultimately, the amount released and delivered to the patient is based on the patient's serum glucose levels. It is important to maintain the serum glucose levels (true) of the patient within acceptable levels (greater than 60 mg/dl and less than 125 mg/100 ml and most preferably to maintain those levels at about 80 mg/100 ml.

Variations in doses are calculated by monitoring serum glucose levels in response to known amounts of insulin released from the device. If the response in decreasing serum glucose level is higher than with previous readings, then the dosage is decreased. If the response in decreasing serum glucose level is lower than with previous readings, then the dosing amount is increased. The increases and decreases are gradual and are preferably based on averages (of 10 or more readings of glucose levels after 10 or more dosing events) and not a single dosing event and monitoring event with respect to serum glucose levels. The present invention can record dosing events and serum glucose levels over time, calculate averages and deduce preferred changes in administration of insulin.

As another feature of the invention, the device can be programmed so as to prevent the administration of more than a given amount of insulin within a given period of time. For example, if the patient normally requires 25 units per day of insulin, the microprocessor of the inhalation device can be programmed to prevent further release of the valve after 35 units has been administered within a given day. Setting a slightly higher limit would allow for the patient to administer additional insulin, if needed, due to larger than normal meals and/or account for misdelivery of insulin such as due to coughing or sneezing during an attempted delivery.

The ability to prevent overdosing is a characteristic of the device due to the ability of the device to monitor the amount of insulin released and calculate the approximate amount of insulin delivered to the patient based on monitoring given events such as airflow rate and serum glucose levels. The ability of the present device to prevent overdosing is not merely a monitoring system which prevents further manual actuation of a button. As indicated above, the device used in connection with the present invention is not manually actuated, but is fired in response to an electrical signal received from a microprocessor. Applicant's device does not allow for the release of insulin merely by the manual actuation of a button to fire a burst of insulin into the air.

The microprocessor of applicant's invention can be designed so as to allow for an override feature which would allow for the administration of additional insulin. The override feature could be actuated in an emergency situation. Alternatively, the override feature could be actuated when the device is electronically connected with a serum glucose level monitoring device which determines that serum glucose levels increase to dangerously high levels.

The microprocessor of applicant's invention will also include a timing device. The timing device can be electrically connected with visual display signals as well as audio alarm signals. Using the timing device, the microprocessor can be programmed so as to allow for a visual or audio signal to be sent when the patient would be normally expected to administer insulin. In addition to indicating the time of administration (preferably by audio signal), the device can indicate the amount of insulin which should be administered by providing a visual display. For example, the audio alarm could sound alerting the patient that insulin should be administered. At the same time, the visual display could indicate "five units" as the amount of insulin to be administered. At this point, a monitoring event could take place. After completion of the monitoring event, administration would proceed and the visual display would continually indicate the remaining amount of insulin which should be administered. After the predetermined dose of five units had been administered, the visual display would indicate that the dosing event had ended. If the patient did not complete the dosing event by administering the stated amount of insulin, the patient would be reminded of such by the initiation of another audio signal, followed by a visual display instructing the patient to continue administration.

Additional information regarding dosing with insulin via injection can be found within Harrison's—Principles of Internal Medicine (most recent edition) published by McGraw Hill Book Company, New York, incorporated herein by reference to disclose conventional information regarding dosing insulin via injection.

Supplemental Treatment Methodology

Patients suffering from diabetes mellitus may be treated solely with insulin as indicated above. However, it is possible to treat such patients with a combination of insulin and other drugs such as sulfonylureas which act primarily by stimulating release of insulin from the beta cells in the pancreas. These drugs have the ability of increasing the number of insulin receptors in target tissues and enhance insulin-mediated glucose disposal. Some specific sulfonylurea drugs which can be used in connection with the present invention include acetohexamide administered in an amount of about 500 to 1,500 mg per day; chlorpropamide, administered in an amount of about 50 to 750 mg per day; tolazamide, administered in an amount of about 0.1 to 1 gram per day; tolbutamide, administered in an amount of about 0.5 to 3 grams per day; glipzide administered in an amount of about 2.5 to 40 mg per day and glyburide administered in an amount of about 1.25 to 20 mg per day.

In patients which are producing some insulin, the sulfonylurea drugs may be sufficient to treat the symptoms. Other patients can use a combination of the drugs while administering insulin, while still others require only the administration of insulin. The present invention is beneficial to each type of patient. Further, the present invention allows means for eliminating the need for some patients to take insulin by injection. The patients can be provided with oral doses of sulfonylureas in amounts similar to those indicated above while administering small amounts of insulin via the intrapulmonary route using the device of the present invention. In accordance with one method of the invention, the patient is administered a sulfonylurea drug orally and that treatment is supplemented with insulin administration in relatively small amounts, e.g., five to ten units per dosing event with two to three dosing events per day. Alternatively, the patient is primarily treated by the administration of insulin via the intrapulmonary route and that treatment is supplemented by the oral administration of sulfonylureas of the type described above.

Based on the above, it will be understood by those skilled in the art that a plurality of different treatments and means of administration can be used to treat a single patient. For example, a patient can be simultaneously treated with insulin by injection, insulin via intrapulmonary administration in accordance with the present invention, and sulfonylurea drugs, which are orally administered. Benefits can be obtained by the oral administration of sulfonylurea drugs in that the insulin is naturally released by the patient in a fashion in accordance with real needs related to serum glucose levels. This natural insulin is supplemented by smaller doses provided by intrapulmonary administration in accordance with the present invention. Should such prove to be ineffective for whatever reason, such as breathing difficulties, such could be supplemented by administration via injection.

Treatment via Insulin Analogs

The methodologies of the present invention can be carried out using any type of insulin, although they are preferably carried out using recombinantly produced human insulin. Insulin extracted from animal sources such as bovine or porcine sources can be used. More recently, insulin analogs have been developed. More specifically, novel proteins have been developed wherein the amino acid sequence of the protein is substantially the same as the amino acid sequence of naturally occurring human insulin but for small changes substituting one amino acid for another. These small changes can have important physiological effects with respect to the treatment of diabetes.

There are two general types of insulin analogs presently used. One type of insulin analog is referred to as superactive insulin. In general, superactive insulin has increased activity over natural human insulin. Accordingly, such insulin can be administered in substantially smaller amounts while obtaining substantially the same effect with respect to reducing serum glucose levels. The other general type of analog is referred to as hepatospecific insulin. Hepatospecific insulin analogs are more active in the liver than in adipose tissue and offer several advantages over currently available insulin therapy. Hepatospecific analogs provide preferential hepatic uptake during peripheral subcutaneous administration, thereby mimicking, more closely, the metabolic balance between the liver and the peripheral tissues. Obtaining the correct metabolic balance is an important part of proper treatment of diabetics and administration via the intrapulmonary route should provide advantages over intermuscular injection with respect to obtaining such a balance. It may be desirable to include mixtures of conventional insulin with insulin which is hepatospecific and/or with superactive insulin analogs. Hepatospecific analogs are disclosed and described within published PCT application WO90/12814, published Nov. 1, 1990, which application is incorporated herein by reference for its disclosure of such hepatospecific insulin analogs and in order to disclose other information cited within the other publications referred to within WO90/12814.

U.S. patent application Ser. No. 074,558 discloses a superactive human insulin analog, [10-Aspartic Acid-B] human insulin, which has increased activity over natural human insulin. Specifically, [10-Aspartic Acid-B] human insulin was determined to be 4 to 5 times more potent than natural insulins. U.S. patent application Ser. No. 273,957 and International application Ser. No. PCT/US88/02289 disclose other superactive insulin analogs, des-pentapeptide (B26-B30)-[Asp$^{B10}$, Tyr$^{B25}$-α-carboxamide] human insulin, (B26-B30)-[Glu$^{B10}$, Tyr$^{B25}$-α-carboxamide] human insulin, and further insulin analogs of the formula des(B26-B30)-[X$^{B10}$, Tyr$^{B25}$-α-carboxamide] human insulin, in which X is a residue substituted at position 10 of the B chain. These insulin analogs have potencies anywhere from 11 to 20 times that of natural human insulin. All of the above-described insulin analogs involve amino acid substitutions along the A or B chains of natural human insulin, which increase the potency of the compound or change other properties of the compound.

Insulin analogs are not presently used for the treatment of patients on a commercial scale. However, a number of different insulin analogs are being developed and the present invention will be particularly applicable with respect to the delivery of such insulin analogs in that the present invention can be used to provide variable dosing in response to currently measured serum glucose levels. Further, since many insulin analogs are more potent than conventional insulin, their delivery via the intrapulmonary route is particularly convenient.

Monitoring Diabetic Control

All methods of treating diabetes involve measuring glucose levels in some manner. Such measurements are necessary in order to titrate proper dosing and avoid the over-administration of insulin which can result in fatal hypoglycemia. Measurements of urine glucose alone are insufficient to assess diabetic control and bring mean plasma glucose values into a near normal range since the urine will be free of glucose when the plasma concentration is relatively normal. For this reason, "home glucose monitoring" is used in those patients treated by continuous subcutaneous insulin infusion (CSII) or multiple subcutaneous injection (MSI) techniques. Such monitoring requires capillary blood which can be obtained in a substantially painless manner using a small spring-triggered device referred to as Autolet™ produced by Ulstr Scientific Incorporated which device is equipped with small disposable lancelets. The amount of glucose is analyzed using chemically impregnated strips which are read in a commercially available reflectance meter. One commercially available strip is referred to as Chemstrip bG (produced by Bio-Dynamics). The Chemstrip bG can provide satisfactory values by visual inspection utilizing a dual-color scale, thus eliminating the need for a reflectance meter. Frequent measurement of the plasma glucose (a fairly standard program utilizes seven or eight assays over a 24-hour period) allows a reasonable assessment of mean plasma glucose levels during the day and guides adjustment of insulin dosage.

The methodology of the present invention is preferably utilized in combination with a closely controlled means of monitoring serum glucose levels. More specifically, the drug delivery device of the invention is used to administer doses of insulin via the intrapulmonary route. The doses may be administered in somewhat smaller amounts than are generally administered by injection. The amount of insulin administered can be readily adjusted in that smaller amounts are generally administered using the intrapulmonary delivery methodology of the present invention. During the day, as insulin is administered, serum glucose levels are frequently monitored. The amount of insulin administered can be dosed based on the monitored serum glucose levels, i.e., as glucose levels increase, the amount of insulin can be increased, and as glucose levels are seen to decrease, the dosing of insulin can be decreased. It will be noted that there is some "lag" time between the administration of a dose of insulin and its effect on serum glucose levels. Accordingly, when glucose levels are seen to increase and insulin is administered, sufficient time should be allowed for the glucose level to decrease prior to the administration of additional insulin in order to avoid overdosing. However, as indicated above, the present device can be readily programmed so as to prevent excessive administration of insulin by programming the microprocessor to not allow the release of the valve if the valve has been released a given number of times within a given period of time. Further, it will be understood that there is generally less "lag" time with intrapulmonary administration as compared to SC injection.

Based on the information disclosed herein in combination with what is known about insulin dosing and serum glucose levels, computer readable programs can be readily developed which can be used in connection with the insulin delivery device of the present invention. More specifically, the microprocessor can be programmed so as to deliver precise doses of insulin which correspond to the particular needs of the patient based on serum glucose monitoring information which is supplied to the microprocessor of the device of the invention. Further, the dosing information contained within the microprocessor of the device of the invention can be fed to a separate computer and/or serum glucose monitoring device (preferably portable) in order to calculate the best treatment and dosing schedule for the particular patient.

Insulin Containing Formulations

A variety of different insulin containing formulations can be used in connection with the present invention. The active ingredient within such formulations is insulin which is preferably recombinantly produced human insulin but, as indicated above, may include insulin extracted from animal sources. Further, the insulin may be an insulin analog which is an analog of human insulin which has been recombinantly produced. Although the insulin and/or analog is generally present by itself as the sole active ingredient, the insulin may be present with an additional active ingredient such as a sulfonylurea. However, such sulfonylureas are generally administered separately in order to more closely control dosing and serum glucose levels.

Regardless of the active ingredient, there are several basic types of insulin formulations which can be used in connection with the present invention. All of the formulations include insulin, preferably with a pharmaceutically acceptable carrier suitable for intrapulmonary administration. In accordance with two preferred formulations, a low boiling point, highly volatile propellant is combined with the active ingredient and a pharmaceutically acceptable excipient. In one of the two formulations, the active ingredient is provided as a suspension or dry powder in the propellant, and in the other formulation, the active ingredient is dissolved in solution within the propellant. Both of these formulations may be readily included within a container which has a valve as its only opening. Since the propellant is highly volatile, i.e., has a low boiling point, the contents of the container will be under pressure.

In accordance with another formulation, the insulin is provided as a dry powder by itself, and in accordance with still another formulation, the insulin or active ingredient is provided in a solution formulation. The dry powder could be directly inhaled by allowing inhalation only at the same measured inspiratory flow rate and inspiratory volume for each delivery. However, the powder is preferably dissolved in an aqueous solvent to create a solution which is moved through a porous membrane to create an aerosol for inhalation.

Figure 2:
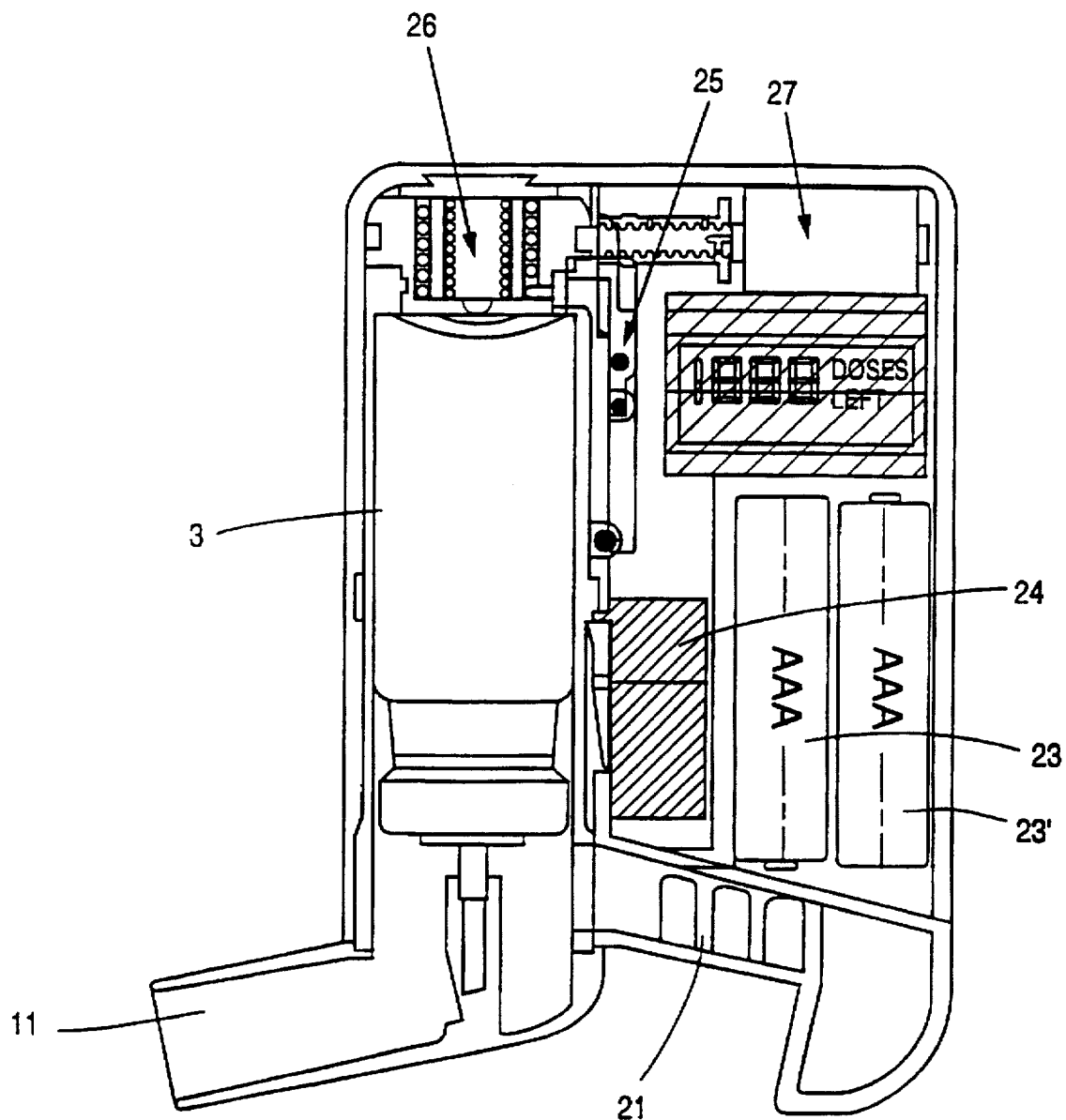
FIG. 2 is another embodiment of an aerosolizing drug delivery device which can be used in the intrapulmonary delivery of insulin in connection with the present invention.

Any formulation which makes it possible to produce aerosolized forms of insulin which can be inhaled and delivered to a patient via the intrapulmonary route can be used in connection with the present invention. Specific information regarding formulations which can be used in connection with aerosolized delivery devices are described within Remington's Pharmaceutical Sciences, A. R. Gennaro editor (latest edition) Mack Publishing Company. Regarding insulin formulations, it is also useful to note Sciarra et al. [Journal of Pharmaceutical Sciences, Vol. 65, No. 4, 1976]. When low boiling point propellants are used, the propellants are held within a pressurized canister of the device and maintained in a liquid state. When the valve is actuated, the propellant is released and forces the active ingredient from the canister along with the propellant. The propellant will "flash" upon exposure to the surrounding atmosphere, i.e., the propellant immediately evaporates. The flashing occurs so rapidly that it is essentially pure active ingredient which is actually delivered to the lungs of the patient. The "flashing" phenomenon which occurs with the use of low boiling point propellants greatly increases the practicality of the present invention as compared with nebulizers or formulations which do not use such propellants in that larger amounts of drug can be easily administered in a short period of time. Further, since the material being delivered to the lungs is essentially pure drug, it is easier to monitor and more closely control dosing which is a critical feature of the methodology of the present invention. Accordingly, when using a delivery device as shown in FIGS. 1 and 2 it is preferable to use low boiling point propellants such as low boiling point chlorofluorocarbons or hydrocarbons, e.g., trichlorofluoromethane and dichlorodifluoromethane. As non-chlorofluorocarbon containing propellants are developed which are low boiling point propellants, their use in connection with the present invention will become apparent to those skilled in the art.

When using a device as per FIGS. 1 and 2, the preferred formulation of the present invention is a suspension formulation wherein a dry powder of insulin is suspended within a low boiling point propellant with an excipient such as oleic acid. Such low boiling point propellants are referred to by conventional nomenclature and two particularly preferred propellants are "P12" and "P114" with a particularly preferred formulation being a 50—50 combination of P12 and P114.

Figure 10:
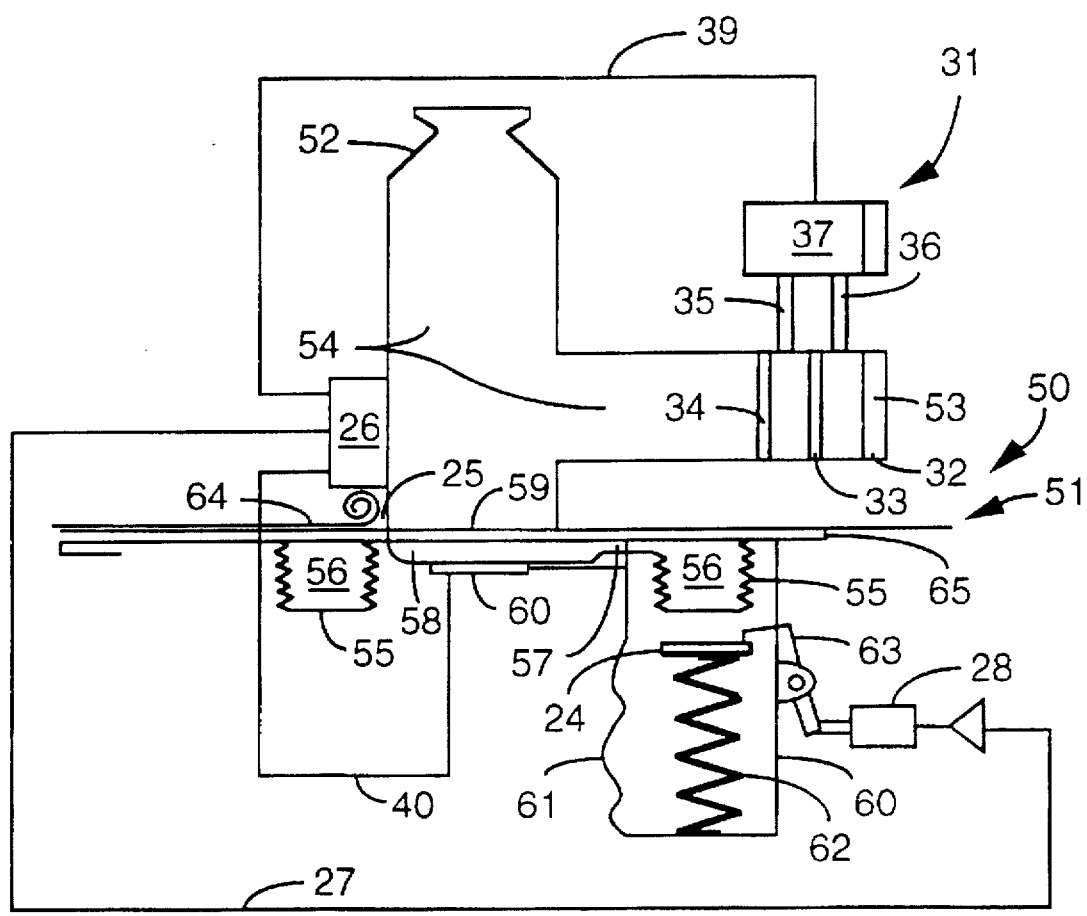
FIG. 10 is a schematic view of another embodiment of an insulin dispensing device.

When using a device as shown in FIG. 10 the insulin is included in a solution such as the type of solution which is made commercially available for injection and/or other solutions which are more acceptable for intrapulmonary delivery. When preparing preferred formulations of the invention which provide for the insulin, excipient and solvent, any pharmaceutically acceptable excipient may be used. Excipients for low boiling point type formulations include compounds such as oleic acid and related oils having a carbon chain length in the range of about 12–30 carbons can be used with oleic acid being particularly preferred.

Formulations include insulin dry powder by itself and/or with an excipient. When such a formulation is used, it may be used in combination with a gas propellant which gas propellant is released over a predetermined amount of dried powder which is forced into the air and inhaled by the patient. It is also possible to design the device so that a predetermined amount of dry powder is placed behind a gate. The gate is opened in the same manner as the valve is released the same inspiratory flow rate and inspiratory volume is repeatedly obtained. Thereafter, the dry powder is inhaled by the patient and the insulin is delivered. When a solution is used the device of FIG. 10 is used to create an aerosolized form of the solution which can be inhaled by the patient.

Formulations of the invention can include liposomes containing insulin in combination with an amount of alveolar surfactant protein effective to enhance the transport of the liposomes across the pulmonary surface and into the circulatory system of the patient. Such liposomes and formulations containing such are disclosed within U.S. Pat. No. 5,006,343, issued Apr. 9, 1991, which is incorporated herein by reference to disclose liposomes and formulations of liposomes used in intrapulmonary delivery. The formulations and methodology disclosed in U.S. Pat. No. 5,006,343 can be adapted for the application of insulin and included within the delivery device of the present invention in order to provide for effective treatments of diabetic patients.

The terms "insulin" and "insulin analog" have been defined above. With respect to both terms, applicant points out that a variety of commercial insulin formulations are available. Rapidly acting preparations are always indicated in diabetic emergencies and in CSII and MSI programs. Intermediate preparations are used in conventional and MSI regimens, and long-acting formulations are used rarely. It is not possible to delineate precisely the biologic responses to the various preparations because peak effects and duration vary from patient to patient and depend not only on route of administration but on dose. The various insulins are available as rapid (regular, semilente), intermediate (NPH, lente, globin), and long-acing (PZI, ultralente) preparations, although not all manufacturers offer all varieties. Lente and NPH insulin are used in most conventional therapy and are roughly equivalent in biologic effects, although lente appears to be slightly more immunogenic and to mix less well with regular insulin than does NPH.

Preferred Flow Rates/Volumes

Figure 5:
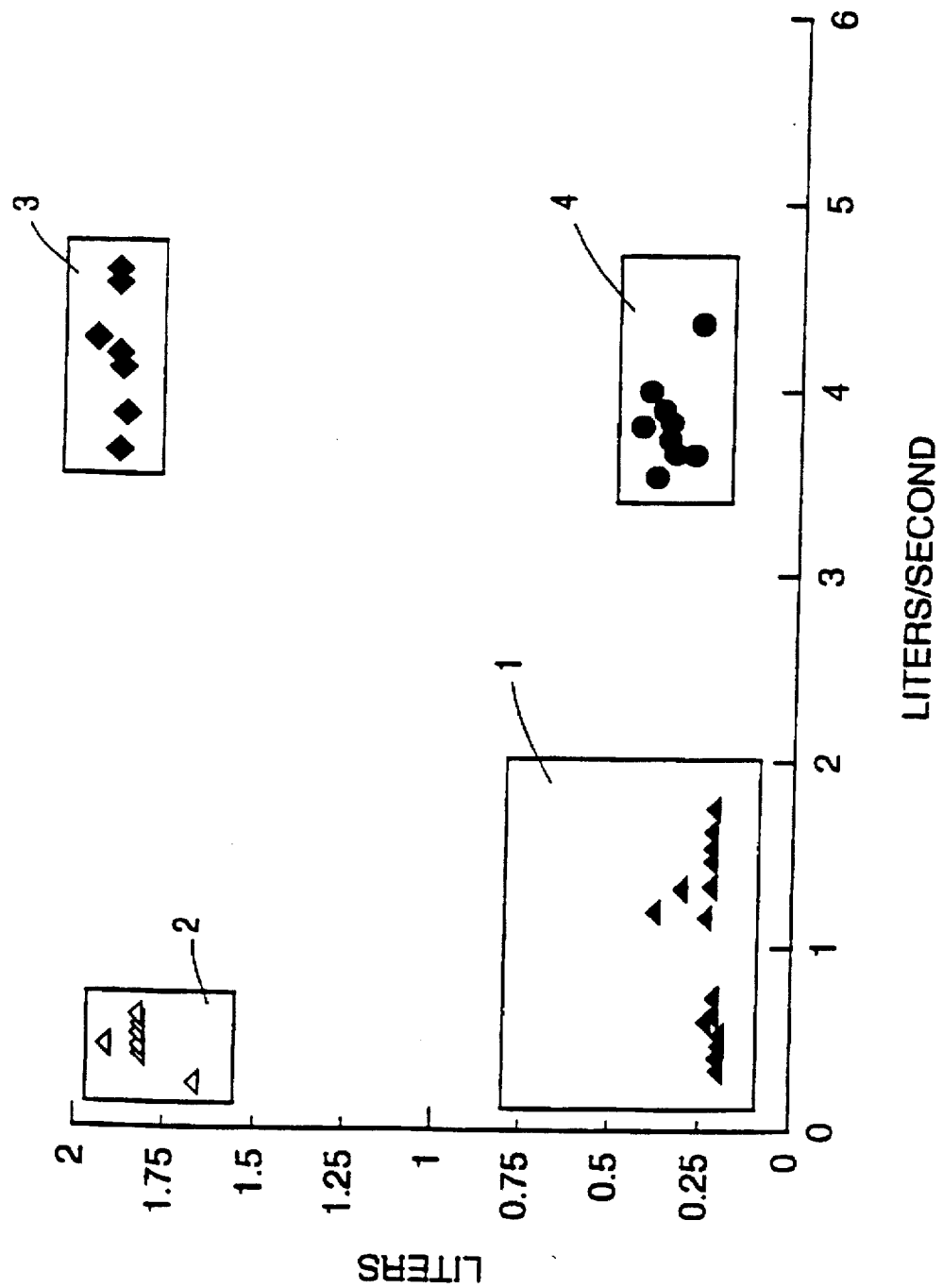
FIG. 5 is a graph showing data points plotted in four general areas with the points plotted relative to inspiratory flow rate (on the abscissa) and inspiratory volume (on the ordinate) in two dimensions.

FIG. 5 is a two-dimensional graph wherein the inspiratory flow rate is plotted against the inspiratory volume. To determine a drug release point the patient's inspiratory flow rate and inspiratory volume may be simultaneously and separately determined, e.g., measured. The measurement is taken and the information obtained from the measurement provided to a microprocessor which microprocessor is programmed to release drug (1) at the same point relative to inspiratory flow and inspiratory volume at each release of drug and (2) to select that point within prescribed parameters of inspiratory flow rates and inspiratory volumes. In the particular results plotted in FIG. 1 the microprocessor was programmed to release drug in four general areas with respect to the inspiratory flow rate and inspiratory volume parameters. This resulted in data points being plotted in four general areas on the two-dimensional graph of FIG. 1. The four areas are labeled 1, 2, 3 and 4. In area 1 (showing solid triangles), the drug was released when the patient's inspiratory flow rate was "slow to medium" (0.10 to 2.0 liters per sec) with an "early" inspiratory volume of 0.15 to 0.8 liters. In area 2 (showing open triangles), the drug was released at a "slow" inspiratory rate/0.10 to 1.0 liters/sec) and a "late" volume (1.6 to 2.8 liters). In area 3 (showing solid diamonds), the drug was released at a "fast" inspiratory flow rate (3.5 to 4.5 liters/sec) and a "late" volume. In area 4 (showing solid circles), the drug was released at a "fast" inspiratory flow rate and an "early" inspiratory volume.

The results shown in FIG. 5 were obtained while administering a radioactively labeled drug to a human. After the administration of the drug it was possible to determine not only the amount of drug, but the pattern of drug deposited within the lungs of the patient. Using this information two conclusions were reached. Firstly, it was determined that it is important to simultaneously and separately consider (in real time) both inspiratory flow rate and inspiratory volume when determining the point for drug release for intrapulmonary drug delivery. Changes in either parameter can greatly effect the amount of drug deposited. Thus, when treating a patient the drug should be released at approximately (±10%, preferably ±5% and most preferable as close as possible to the first release point) the same inspiratory flow rate and inspiratory volume each time—going back to the same point each time for the same patient ensures repeatable dosing. In practice the tighter the point is defined the greater the repeatability of dosing. However, if the point is defined to precisely it can be difficult for the patient to obtain that rate/volume point again. Thus, some degree of tolerance is generally applied. Secondly, it was found that within particular ranges with respect to inspiratory flow rate and inspiratory volume it was possible to obtain a consistently high percentage amount of drug deposited in the lung. Such results are shown graphically within the three dimensional graph as shown in FIG. 6.

Figure 6:
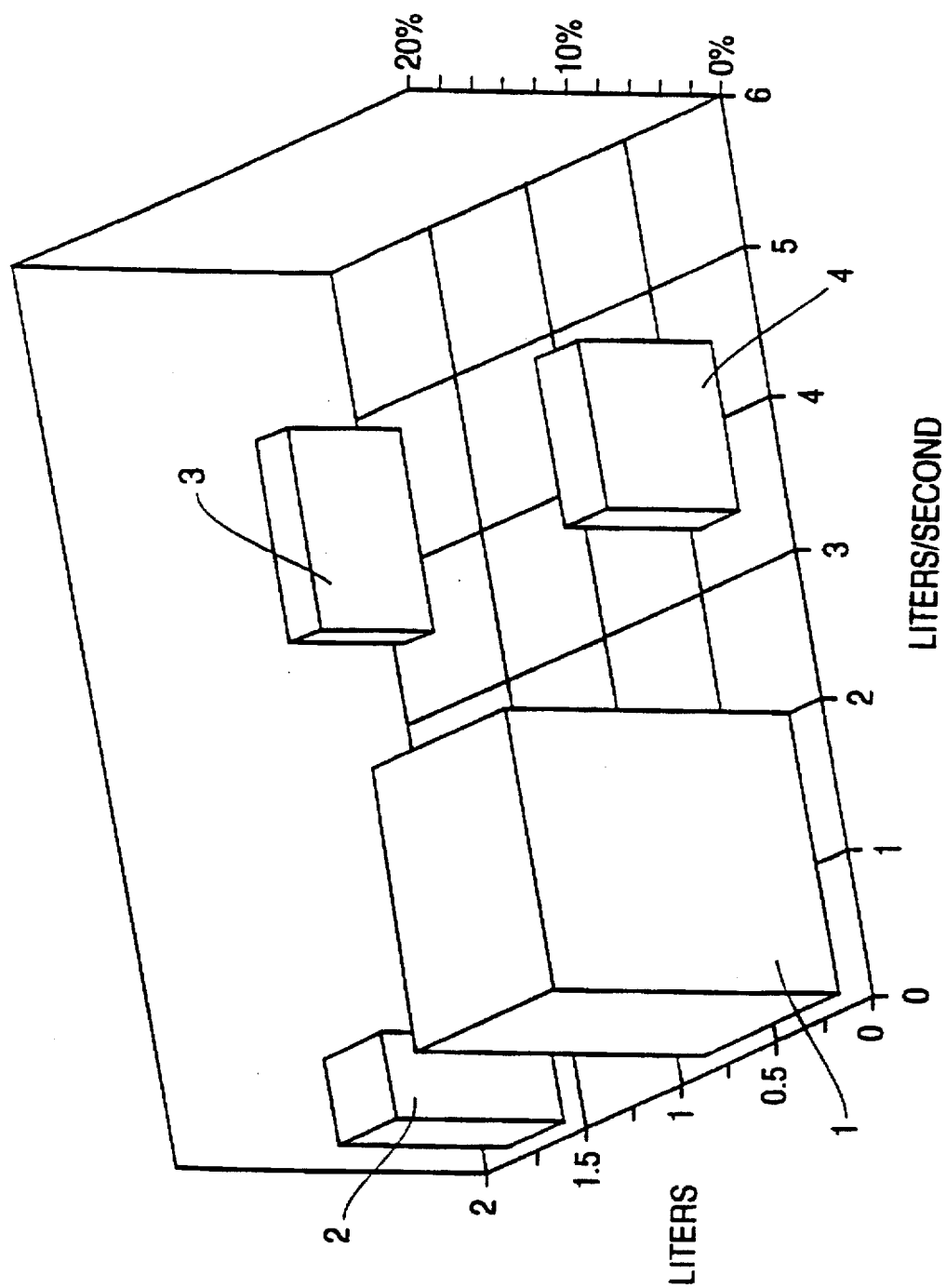
FIG. 6 is a graph showing the four general areas plotted per FIG. 1 now plotted with a third dimension to show the percentage of drug reaching the lungs based on a constant amount of drug released.

The third dimension as shown in FIG. 6 (the height of the four columns) indicates the percentage amount of drug deposited based on the total amount of drug released to the patient. The area labeled 1 clearly showed the highest percentage of drug delivered to the patient based on the amount of drug released. Using this information it was possible to calculate a specific area regarding inspiratory flow rate and inspiratory volume at which it is possible to obtain not only a high degree of repeatability in dosing, but obtain a higher percentage of drug being delivered based on the percentage of drug released. Specifically, it was determined that the drug should be released within inspiratory flow rate range of 0.10 to 2.0 liters per second and at an inspiratory volume in the range of about 0.15 to about 0.80 liters. This range is shown by the rectangularly shaped column of FIG. 7.

In that intrapulmonary drug delivery systems often provide for erratic dosing it is important to provide a method which allows for consistent, repeatable dosing. This is obtained by simultaneously and separately considering both inspiratory flow rate and inspiratory volume in order to define a point by its abscissa and ordinate. If both measurements are separately considered the drug can be released anywhere along the abscissa and ordinate scales shown in FIG. 5. Once a point is selected (such as by randomly selecting a point in box 1 of the graph of FIG. 5) that selected point (with the same coordinants) is used again and again by a given patient to obtain repeatable dosing. If only one parameter is measured (abscissa or ordinate) and drug is released based on that parameter the drug release point is defined by a line on the graph of FIG. 5. When drug is released again the release can be at any point on that line. For example, the inspiratory flow rate (measured horizontally on the abscissa) might be defined by a point. However, the inspiratory volume (which was not measured and/or considered) would be defined only by a vertical line. Thus, subsequent releases would be at different volumes along that vertical line and the dosing would not be consistent. By measuring both inspiratory flow rate on the abscissa and inspiratory volume on the ordinant the coordinants will mark a point for drug release. That point can be found again and again to obtain repeatability in dosing. The same point should be selected each time as closely as possible and within a margin of errors of ±10% with respect to each criteria. The margin for error can be increased and still maintain acceptable levels of repeatable dosing—but the error should keep the drug release point inside the box 1 of FIG. 5.

Figure 7:
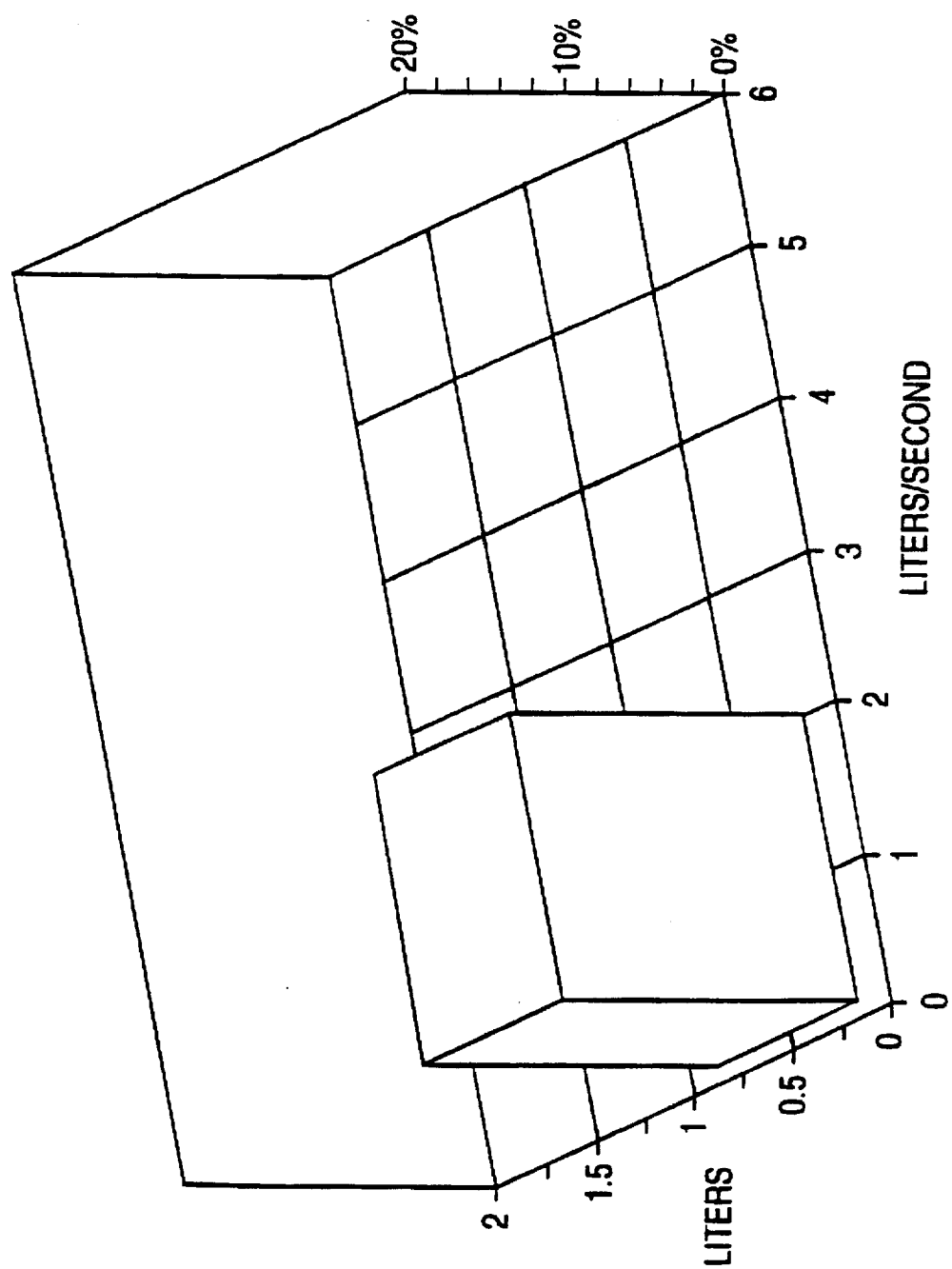
FIG. 7 is a three dimensional graph showing the therapeutic values for inspiratory flow rate and inspiratory volume which provide better drug delivery efficiency.
Figure 8:
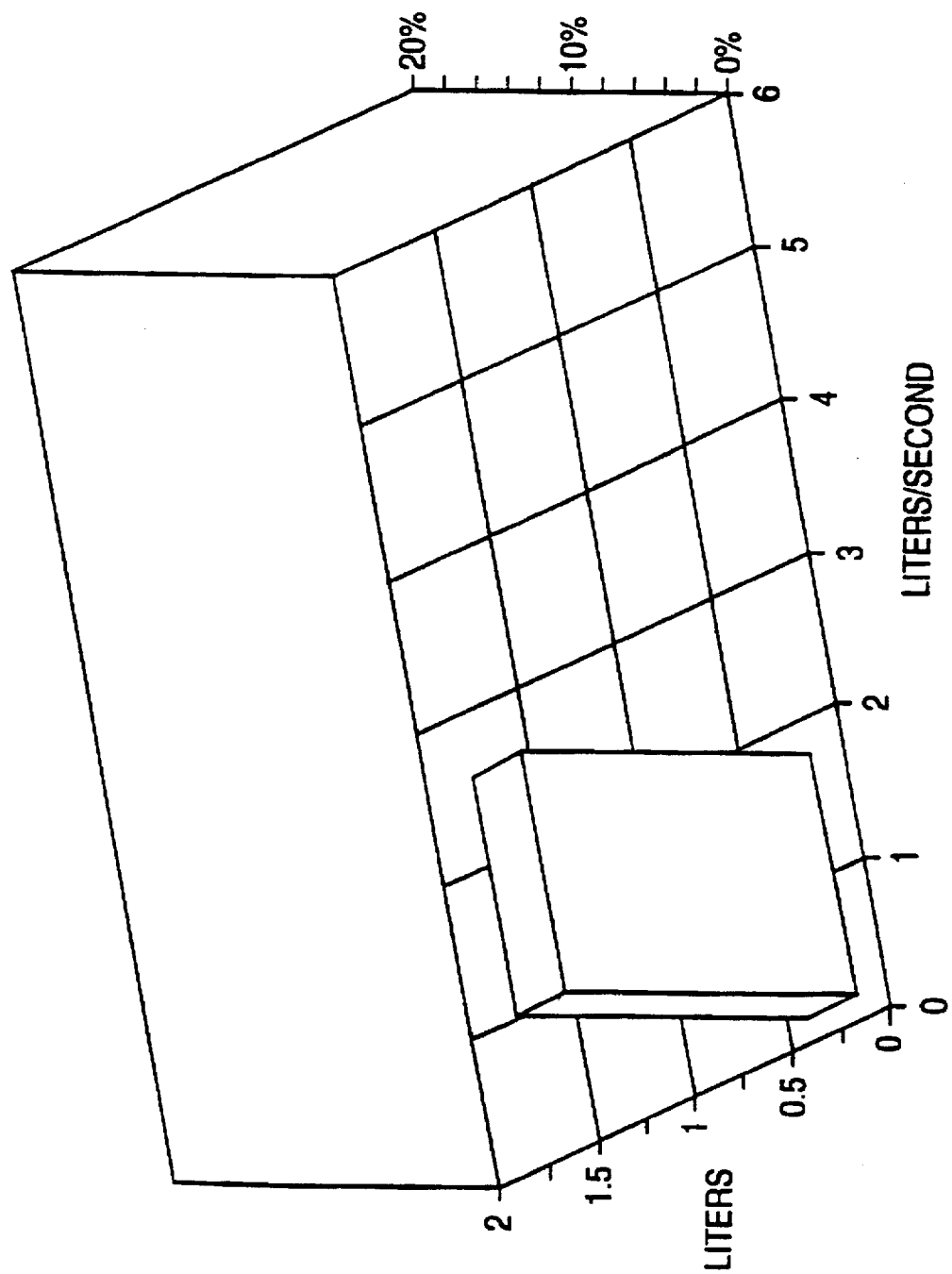
FIG. 8 shows a preferred range of the valves shown in FIG. 7.
Figure 9:
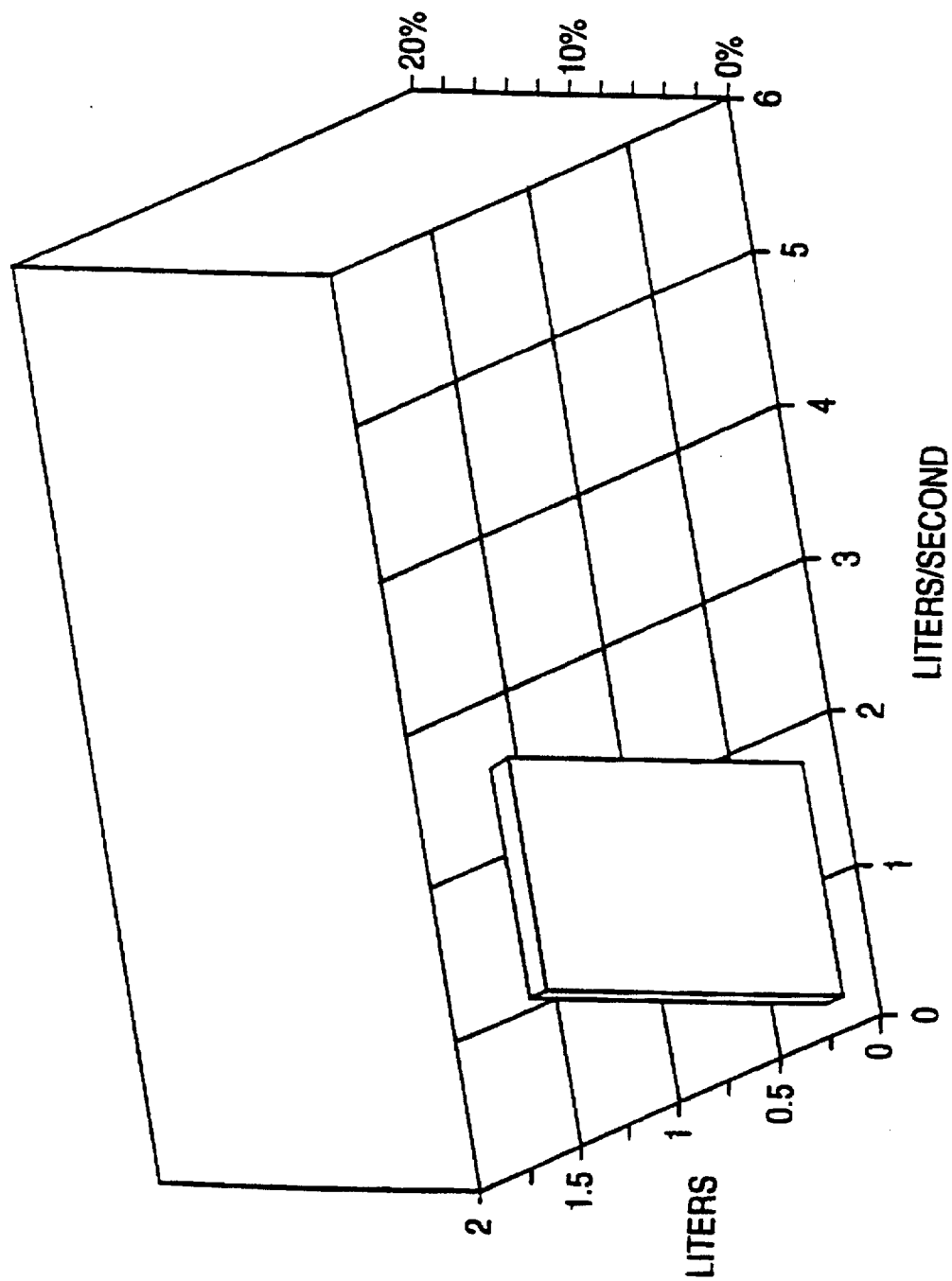
FIG. 9 shows a particularly preferred range for the valves of FIG. 7.

By examining delivery of drug associated with the data points plotted in FIG. 5, it is possible to determine a preferred and particularly preferred and most preferred range as per FIGS. 7, 8 and 9. The preferred range of FIG. 7 shows drug released at a volume of 0.15 to 0.8 liters and rate of 0.10 to 2.0 liters/second. The particularly preferred range plotted in FIG. 8 indicates that the inspiratory flow should be within the range of 0.2 to about 1.8 liters per second with an inspiratory volume in the range of 0.15 to about 0.4 liters. The most preferred range (FIG. 9) is from about 0.15 to about 1.8 liters per second for the inspiratory flow rate and about 0.15 to about 0.25 liters for the inspiratory volume. Thus, preferred delivery can be obtained by (1) repeatedly delivering aerosolized formulation to a patient at the same simultaneously and separately measured inspiratory flow rate and inspiratory volume and (2) releasing drug to the patient within specified therapeutically effective ranges as shown within FIGS. 7, 8 and 9. The invention involves releasing drug (after measuring) inside the ranges as per FIGS. 7, 8 or 9. Thus, the release could begin inside or outside the range. Preferably the drug release begins inside the range and more preferable begins and ends inside the ranges of FIGS. 7, 8 or 9.

The methodology of the invention may be carried out using a portable, hand-held, battery-powered device. As per U.S. patent application Ser. No. 08/002,507 filed Jan. 29, 1993 incorporated herein by reference. In accordance with another system the methodology of the invention could be carried out using the device, dosage units and system disclosed in U.S. patent application Ser. No. 08/247,012 filed May 20, 1994. In accordance with the system the insulin drug (which is preferably recombinant insulin) is included in an aqueous formulation which is aerosolized by moving the formulation through a porous membrane. Alternatively, the methodology of the invention could be carried out using a mechanical (non-electronic) device. Those skilled in the art recognized that various components can be mechanical set to actuate at a given inspiratory flow rate (e.g. a spring biased valve) and at a given volume (e.g.

a spinable flywheel which rotates a given amount per a given volume). The components of such devices could be set to allow drug release inside the parameters of FIGS. 3, 4 or 5.

The insulin which is released to the patient may be in a variety of different forms. For example, the insulin may be an aqueous solution of drug, i.e., drug dissolved in water and formed into small particles to create an aerosol which is delivered to the patient. Alternatively, the drug may be in a solution wherein a low-boiling point propellant is used as a solvent. In yet, another embodiment the insulin may be in the form of a dry powder which is intermixed with an airflow in order to provide for particlized delivery of drug to the patient. Regardless of the type of drug or the form of the drug formulation, it is preferable to create drug particles having a size in the range of about 0.5 to 12 microns. By creating drug particles which have a relatively narrow range of size, it is possible to further increase the efficiency of the drug delivery system and improve the repeatability of the dosing. Thus, it is preferable that the particles not only have a size in the range of 0.5 to 12 microns but that the mean particle size be within a narrow range so that 80% or more of the particles being delivered to a patient have a particle diameter which is within ±20% of the average particle size, preferably ±10% and more preferably ±5% of the average particle size.

The velocity at which the aerosolized drug is released to the patient is also important in terms of obtaining a high degree of repeatability in dosing and providing for a high percentage of drug being delivered to the patient's lungs. Most preferably, the drug is released from a container in a direction which is normal to the patient's airflow. Accordingly, the drug may be released directly upward so that its flow is at a 90° angle with respect to the patient's inspiratory flow which is directly horizontal. After being released, the drug velocity decreases and the drug particles remain suspended for a sufficient period of time to allow the patient's inspiration to draw the drug into the patient's lungs. The velocity of drug released in the direction from the drug release point to the patient may match the patient's inspiratory flow rate but is preferably slower that the patient's inspiratory flow rate and is most preferably about zero. The velocity may be slightly negative, i.e., in a direction away from the patient. The velocity may range from –2.0 liters/sec to 2.0 liters/sec and is preferably zero. It is not desirable to project the drug toward the patient at a rate above the speed of the patient's breath as such may result in drug being deposited on the back of the patient's throat. Thus, the drug release speed should be equal to or less than the breath speed. The actual speed of release can vary depending on factors such as the particle size, the particle composition and the distance between the point of release and the patient. The velocity is preferably such that the particles will (due to air resistance) slow to zero velocity after traveling a distance of about 2 centimeters or less. In general, the shorter the distance required to slow the particles to zero velocity the better.

An aerosol may be created by forcing drug through pores of a membrane which pores have a size in the range of about 0.25 to 6 microns. When the pores have this size the particles which escape through the pores to create the aerosol will have a diameter in the range of 0.5 to 12 microns. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that the object is to provide aerosolized particles having a diameter in the range of about 0.5 to 12 microns.

The drug formulation may be a low viscosity liquid formulation. The viscosity of the drug by itself or in combination with a carrier must be sufficiently low so that the formulation can be forced out of openings to form an aerosol, e.g., using 20 to 200 psi to form an aerosol preferably having a particle size in the range of about 0.5 to 12 microns.

Drug may be stored in and/or released from a container of any desired size. In most cases the size of the container is not directly related to the amount of drug being delivered in that most formulations include relatively large amounts of excipient material e.g. water or a saline solution. Accordingly, a given size container could include a wide range of different doses by varying drug concentration.

Drug containers may include indices which may be electronic and may be connected to a power source such as a battery. When the indices are in the form of visually perceivable numbers, letters or any type of symbol capable of conveying information to the patient. Alternatively, the indices may be connected to a power source such as a battery when the indices are in the form of magnetically, optically or electronically recorded information which can be read by a drug dispensing device which in turn provides visual or audio information to the user. The indices can be designed for any desired purpose but in general provides specific information relating to the day and/or time which the drug within a container should be administered to the patient. Such indices may record, store and transfer information to a drug dispensing device regarding the number of doses remaining in the container. The containers may include labeling which can be in any format and could include days of the month or other symbols or numbers in any variation or language.

In addition to disclosing specific information regarding the day and time for drug delivery the indices could provide more detailed information such as the amount of drug dispensed from each container which might be particularly useful if the containers included different amounts of drug. Further, magnetic, optical and/or electronic indices could have new information recorded onto them which information could be placed there by the drug dispensing device. For example, a magnetic recording means could receive information from the drug dispensing device indicating the precise time which the drug was actually administered to the patient. In addition to recording the time of delivery the device could monitor the expected efficacy of the delivery based on factors such as the inspiratory flow rate which occurred following the initial release of drug. The information recorded could then be read by a separate device, interpreted by the care-giver and used to determine the usefulness of the present treatment methodology. For example, if the glucose levels of the patient did not appear to be responding well but the recorded information indicating that the patient had taken the drug at the wrong time or that the patient had misdelivered drug by changing inspiratory flow rate after initial release it might be determined that further education in patient use of the device was needed but that the present dosing methodology might well be useful. However, if the recordings indicated that the patient had delivered the drug using the proper techniques and still not obtained the correct results acceptable glucose levels) another dosing methodology might be recommended.

The method of managing a patient's pain may be carried out using a hand-held, portable device comprised of (a) a device for holding a disposable package comprised of at least one but preferably a number of drug containers, (b) a propellant or a mechanical mechanism for moving the contents of a container through a porous membrane (c) a monitor for analyzing the inspiratory flow, rate and volume of a patient, and (d) a switch for automatically releasing or firing the mechanical means after the inspiratory flow and/or volume reaches a threshold level. The device may also include a transport mechanism to move the package from one container to the next. The entire device is self-contained, light weight (less than 1 kg preferably less than 0.5 kg loaded) and portable.

The device may include a mouth piece at the end of the flow path, and the patient inhales from the mouth piece which causes an inspiratory flow to be measured within the flow path which path may be in a non-linear flow-pressure relationship. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means (and/or a vibration device below the resonance cavity). When the actuation means is signaled, it causes the mechanical means (by pressure or vibration) to move drug from a container on the package into the inspiratory flow path of the device and ultimately into the patient's lungs. After being released, the drug and carrier will pass through a porous membrane which is vibrated to aerosolize the formulation and thereafter the lungs of the patient. Containers and systems of the type described above are disclosed and described in U.S. patent application Ser. No. 08/247,012 filed May 20, 1994 which is incorporated herein by reference to disclose and describe such containers and systems.

It is important to note that the firing threshold of the device is not based on a single criterion such as the rate of air flow through the device or a specific time after the patient begins inhalation. The firing threshold is based on repeating the firing at the same flow rate and volume as per FIGS. 5–9. This means that the microprocessor controlling the device takes into consideration the instantaneous air flow rate as well as the cumulative inspiratory flow volume. Both are simultaneously considered together in order to determine the optimal point in the patient's inspiratory cycle most preferable in terms of (1) reproducibly delivering the same amount of drug to the patient with each release of drug by releasing drug at the same point each time and maximizing the amount of drug delivered as a percentage of the total amount of drug released by releasing with the parameters described herein.

The device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means on the disposable package.

The details of a drug delivery device which includes a microprocessor and pressure transducer of the type used in connection with the present invention are described and disclosed within U.S. patent application Ser. No. 07/664,758 filed on Mar. 5, 1991 entitled "Delivery of Aerosol Medications for Inspiration" which application is incorporated in its entirety herein by reference, and it is specifically incorporated in order to describe and disclose the microprocessor and program technology used therewith. (See also PCT application 92-01815 also incorporated by reference.)

The use of such a microprocessor with a drug delivery device is disclosed in our earlier filed U.S. patent application Ser. No. 08/065,660 filed May 21, 1993 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, a microprocessor, containing read only memory which in turn contains the pre-programmed information, is plugged into the device. For each of these three embodiments, changing the programming of the memory device readable by a microprocessor will radically change the behavior of the device by causing the microprocessor to be programmed in a different manner. This is done to accommodate different drugs for different types of treatment.

In a preferred embodiment of the methodology of the invention several different criteria are considered. (1) The inspiratory flow rate and inspiratory volume are simultaneously and separately measured to insure repeatability. (2) The drug is released inside the parameters of FIGS. 7, 8 or 9 with FIG. 9 parameters being most preferred. (3) The particle size of the released drug is in the range of 0.5 to 12 microns and 80% or more and the particles have the same size as the average particle size ±10% in size. (4) The drug particles are released at a velocity which is obtained at a flow rate in the range of greater than −2.0 liters/sec. and less than 2.0 liters/sec. As indicated early the actual velocity can vary based on a number of factors. The release velocity should be determined so that the particles are at or are slowed to zero velocity after traveling about 0.5 to 2 cm from the release point. The speed being measured from the drug release point in a direction toward the back of the throat of the patient.

After dosing a patient with insulin it is desirable to take blood samples, measure glucose and make adjustments as needed to obtain the desired glucose level. In accordance with all methods the patient does not push a button to release drug. The drug is released automatically by signals from the microprocessor using measurements obtained.

These doses are based on the assumption that when interpulmonary delivery methodology is used the efficiency of the delivery is approximately 10% and adjustments in the amount released must be made in order to take into account the efficiency of the device. The differential between the amount of insulin actually released from the device and the amount actually delivered to the patient varies due to a number of factors. In general, devices used with the present invention can have an efficiency as low as 10% and as high as 50% meaning that as little as 10% of the released insulin may actually reach the circulatory system of the patient and as much as 50% might be delivered. The efficiency of the delivery will vary somewhat from patient to patient and must be taken into account when programming the device for the release of insulin. In general, a conventional metered dose inhaling device is about 10% efficient.

One of the important features and advantages of the present invention is that the microprocessor can be programmed to take two different criteria into consideration with respect to dosing times. Specifically, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than 5 units of insulin within one hour. More importantly, the device can be programmed to take both criteria into consideration. Thus, the device can be programmed to include a minimum time interval between doses and a maximum amount of insulin to be released within a given time period. For example, the microprocessor could be programmed to allow the release of a maximum of 5 units of insulin during an hour which could only be released in amounts of 1 unit with each release being separated by a minimum of five minutes.

The dosing program can be designed with some flexibility. For example, if the patient normally requires 25 units of insulin per day, the microprocessor of the inhalation device can be programmed to prevent further release of the valve after 35 units have been administered within a given day. Setting a slightly higher limit would allow for the patient to administer additional insulin, if needed, due to a higher food intake and/or to account for misdelivery of insulin such as due to coughing or sneezing during an attempted delivery.

The ability to prevent overdosing is a characteristic of the device due to the ability of the device to monitor the amount of insulin released and calculate the approximate amount of insulin delivered to the patient based on monitoring given events such as the glucose levels. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a inspiratory cycle. When using the present invention, each release of the valve is a release which will administer drug to the patient in that the valve is released in response to patient inhalation. More specifically, the device does not allow for the release of insulin merely by the manual actuation of a button to fire a burst of insulin into the air or a container.

The microprocessor of applicant's invention will also include a timing device. The timing device can be electrically connected with visual display signals as well as audio alarm signals. Using the timing device, the microprocessor can be programmed so as to allow for a visual or audio signal to be sent when the patient would be normally expected to administer insulin. In addition to indicating the time of administration (preferably by audio signal), the device can indicate the amount of insulin which should be administered by providing a visual display. For example, the audio alarm could sound alerting the patient that insulin should be administered. At the same time, the visual display could indicate "50 units" as the amount of insulin drug to be administered. At this point, a monitoring event could take place. After completion of the monitoring event, administration would proceed and the visual display would continually indicate the remaining amount of insulin which should be administered. After the predetermined dose of 5 units had been administered, the visual display would indicate that the dosing event had ended. If the patient did not complete the dosing event by administering the stated amount of insulin, the patient would be reminded of such by the initiation of another audio signal, followed by a visual display instructing the patient to continue administration.

Additional information regarding dosing with insulin via injection can be found within Harrison's—Principles of Internal Medicine (most recent edition) published by McGraw Hill Book Company, New York, incorporated herein by reference to disclose conventional information regarding dosing insulin via injection.

Delivery Device

There are two preferred types of devices which can be used with the present invention. In general, one type uses a low boiling point propellant and the other uses aqueous formulations. The devices which use low boiling point propellants are shown in FIGS. 1–4 and an embodiment of a device which uses aqueous formulations is shown in FIG. 10. Regardless of which type is used the device is a hand-held, portable device which is comprised of (a) a means for separately measuring and analyzing the inspiratory flow rate and inspiratory volume of a patient and (b) a means for automatically releasing a measured amount of insulin into the inspiratory flow path of a patient, e.g. an automatic valve actuation means or mechanism for moving formulation through a porous membrane. In order to use the device, the device must be "loaded", i.e. connected to (c) a source of insulin which, in general, is a recombinantly produced insulin in water or in a low boiling point propellant. The entire device is light weight (less than 1 kg loaded) and portable.

A formulation of insulin in a low boiling point propellant is typically contained in a pressurized canister which is connectable to the "unloaded" device, i.e., the device without the container. When the container of propellant and insulin is connected to the device, the container will include a valve opening at one end which opening is seated into a flow path within the device. The device preferably includes a mouth piece at the end of the flow path, and the patient inhales from the mouth piece which causes an inspiratory flow to be measured within the flow path. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means. When the actuation means is signaled, it releases a valve allowing insulin and propellant to escape into the inspiratory flow path of the device and ultimately into the patient's lungs. After being released, the drug and propellant will preferably pass through a nozzle prior to entering the inspiratory flow path of the device and thereafter the lungs of the patient.

It is important to note that the firing threshold of the device is not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume when it determines the optimal point in the patient's inspiratory cycle which would be most preferable in terms of reproducibly delivering the same amount of drug to the patient with each release of drug. The high degree of dosing repeatability needed to deliver insulin may be obtained merely by measuring and releasing at the same measured flow rate and volume for each release of drug. Further, the device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time.

FIG. 1 shows a cross-sectional view of a hand-held, portable, electronic breath-actuated inhaler device which can be used in connection with the present invention. The device is shown with a holder 1 having cylindrical side walls and a removable cap. The holder 1 is "loaded" in that it includes the pressurized canister 3. The canister 3 includes a non-metering valve 5 which is held down in the open position when the cap 2 is screwed down, thus setting the valve 5 into a seat 6 which is in connection with a flow path 8.

A formulation 4 comprised of insulin and a suitable propellant, such as a low boiling point propellant, is contained within the pressurized canister 3. Propellant and insulin are released from the canister 3 via the electrically controlled solenoid 7. In that the valve 5 of the canister is continuously open, another valve, contained within solenoid 7, facilitates the release of the drug. When the solenoid 7 allows release of propellant and drug, the propellant and drug flows through the flow path 8 and then through the solenoid actuated valve 9 into the flow path 10, out through the nozzle 13 and then into the inspiratory flow path 11 surrounded by walls 12.

It is important to note that a variety of devices can be used in order to carry out delivery methodology of the present invention. However, the device must be capable of allowing the release of a metered amount of aerosolized insulin based on pre-programmed criteria relating to flow rate and volume. These measurements may be made mechanically but are preferable electronic and are readable by the microprocessor 22. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 22, containing read only memory which in turn contains the pre-programmed information, is plugged into the device. For each of these three embodiments, changing the programming of the memory device readable by microprocessor 22 will radically change the behavior of the device by causing microprocessor 22 to be programmed in a different manner. As regards the present invention, the non-volatile memory may contain information relevant only to the administration of insulin to a specific patient. Microprocessor 22 sends signals to solenoid 7 which determines the amount of drug delivered into the inspiratory flow path. Further, microprocessor 22 keeps a record of all drug dosing times and amounts using a read/write non-volatile memory which is in turn readable by an external device. The formulation 4 contained within canister 3 is released into the atmosphere ultimately via nozzle 13 which opens into inspiratory flow path 11. It is at this point that the low boiling point propellant within formulation 4 flashes, i.e. rapidly evaporates, thus providing particles of insulin in an aerosol which is introduced into the mouth and then into the lungs of the patient. In order to allow for ease of use, it is possible to form inspiratory flow path 11 into a mouth piece which can be specifically designed to fit the mouth of a particular patient using the device.

The solenoid 7, and associated valve 9, flow paths 8 and 10, as well as nozzle 13 make up the aerosol delivery system 14 shown by the dotted lines within FIG. 1. The system 14 is in connection with the flow sensor 15 which is capable of measuring a flow rate of about 0 to about 300 liters per minute. The flow sensor 15 includes screens 16, 17 and 18 which are positioned approximately ¼" apart from each other. Tubes 19 and 20 open to the area between the screens 16, 17 and 18 with the tubes 19 and 20 being connected to a conventional differential pressure transducer 21. When the user draws air through inspiratory flow path 11, air is passed through the screens 16, 17 and 18 and the air flow can be measured by the differential air pressure transducer 21. The flow sensor 15 is in connection with the aerosol delivery system 14, and when a threshold value of air flow is reached, the aerosol delivery system 14 allows the release of formulation 4 so that a controlled amount of insulin is delivered to the patient. Solenoid 7 is connected to a microprocessor 22 via an electrical connection. The details of the microprocessor and the details of other drug delivery devices which might be used in connection with the present invention are described and disclosed within U.S. patent application Ser. No. 07/664,758, filed on Mar. 5, 1991 entitled "Delivery of Aerosol Medications for Inspiration" which application is incorporated in its entirety herein by reference, and it is specifically incorporated in order to describe and disclose devices as shown within FIG. 1 and the microprocessor and program technology used therewith.

A cross-sectional view of yet another (and more preferred) embodiment of the hand-held, electronic, breath-actuated inhaler device of the invention is shown in FIG. 2. The device of FIG. 2 shows all of the components present within the single hand-held, portable device, i.e. the power source not shown in FIG. 1 is shown in the device in FIG. 2. Like the device shown within FIG. 1, the device of FIG. 2 includes a canister 3 which includes a canister valve 5. However, unlike the device of FIG. 1, the device of FIG. 2 does not have the valve continuously open but allows a valve 5 connected to the canister 3 to be opened by the mechanical force generated by a valve actuation mechanism 26 which is a motor driven, mechanical mechanism powered by a power source such as batteries 23 and 23'. However, like the device shown within FIG. 1, the patient inhales through inspiratory flow path 11 which can form a mouth piece in order to obtain a metering event using the differential pressure transducer 21. Further, when the inspiratory flow meets a threshold of a pre-programmed criteria, the microprocessor 24 sends a signal to an actuator release mechanism 25 which actuates the actuation mechanism 26 forcing canister 3 downward so that canister valve 5 releases formulation into the inspiratory flow path 11. Further details regarding the device of FIG. 2 are described within co-pending U.S. patent application entitled "An Automatic Aerosol Medication Delivery System and Methods", filed on Jan. 29, 1993 as Ser. No. 08/002,507, which application is incorporated herein by reference in its entirety and specifically incorporated in order to describe and disclose devices as shown within FIG. 2 and the microprocessor and program technology used therewith.

Microprocessor 24 of FIG. 2 includes an external non-volatile read/write memory subsystem, peripheral devices to support this memory system, reset circuit, a clock oscillator, a data acquisition subsystem and an LCD annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of insulin to a patient upon actuation. Adjustments can be made in the program so that when the patient's inspiratory flow profile is changed such is taken into consideration. This can be done by allowing the patient to inhale through the device as a test in order to measure air flow with preferred drug delivery points determined based on the results of several inhalations by each particular patient. This process can be readily repeated when the inspiratory flow profile is changed for whatever reason, e.g. abdominal incisional pain resulting in low tidal volumes. Determination of optimal drug delivery points in the inspiratory flow can be done at each dosing event, daily, weekly, or with the replacement of a new canister in the device.

The microprocessor of the present invention, along with its associated peripheral devices, can be programmed so as to prevent the release of drug from the canister from occurring more than a given number of times within a given period of time. This feature makes it possible to prevent overdosing the patient with too much insulin. The overdose prevention feature can be particularly designed with each individual patient in mind or designed with particular groups of patients in mind. For example, the microprocessor can be programmed so as to prevent the release of more than approximately 25 units of insulin per day when the patient is normally dosed with approximately 20 units of insulin per day. The systems can also be designed so that only a given amount of insulin is provided at a given dosing event. For example, the system can be designed so that only approximately 10 units of insulin is given in a given 15-minute period over which the patient will make approximately 10 inhalations with one unit of insulin being delivered with each inhalation. By providing this feature, greater assurances are obtained with respect to delivering the insulin gradually over time and thereby maintaining a desired glucose level.

Another feature of the device is that it may be programmed to not release drug if it does not receive a signal transmitted to it by a transmitter worn by the intended user. Such a system improves the security of the device and prevents misuse by unauthorized users such as children.

The microprocessor of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices such as a glucose monitoring device. All of the features of the invention are provided in a portable, programmable, battery-powered, hand-held device for patient use which has a size which compares favorably with existing metered dose inhaler devices.

Different mechanisms will be necessary in order to deliver different formulations, such as a dry powder without any propellant. A device could be readily designed so as to provide for the mechanical movement of a predetermined amount of dry powder to a given area. The dry powder would be concealed by a gate, which gate would be opened in the same manner described above, i.e., it would be opened when a predetermined flow rate level and cumulative volume have been achieved based on an earlier monitoring event. Patient inhalation would then cause the dry powder to form a dry dust cloud and be inhaled. Dry powder can also be aerosolized by compressed gas, and a solution can be aerosolized by a compressed gas released in a similar manner and then inhaled.

In addition to monitoring serum glucose levels in order to determine proper insulin dosing, the microprocessor of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the valve when the inhalation cycle is repeated during the dosing event. The devices of FIGS. 1 and 2 have been put forth in connection with devices which use a low boiling point propellant and preferably use that propellant in combination with a suspension formulation which includes the dry powdered insulin within the low-boiling-point propellant. Those skilled in the art will readily recognize that such devices can be used for administering a solution of insulin within the low-boiling-point propellant. However, those skilled in the art will also readily recognize that different mechanisms will be necessary in order to deliver different formulations, such as a dry powder without any propellant. A device could be readily designed so as to provide for the mechanical movement of a predetermined amount of dry powder to a given area. The dry powder would be concealed by a gate, which gate would be opened in the same manner described above, i.e., it would be opened when a predetermined flow rate level and cumulative volume have been achieved based on an earlier monitoring event. Patient inhalation would then cause the dry powder to form a dry dust cloud and be inhaled. Dry powder can also be aerosolized by compressed gas, and a solution can be aerosolized by a compressed gas released in a similar manner and then inhaled.

Aqueous System Device

The device of FIGS. 1 and 2 can be used to deliver a formulation of insulin and low boiling point propellant. The system shown in FIG. 10 is used to deliver a formulation of insulin in a carrier of water and/or ethanol. An embodiment of such a device will now be described in detail.

The device 50 shown in FIG. 10 is loaded with a disposable package 51. To use the device 50 a patient (not shown) inhales air from the mouthpiece 52. The air drawn in through the opening 53 and flows through the flow path The package 51 is comprised of a plurality of containers 55. Each container 55 includes a drug formulation 56 and is in fluid connection via a channel 57 with the cavity 58. The cavity 58 is covered by the porous membrane 59. A vibration device 60 may be positioned directly below the cavity 58.

The device 50 is a hand-held, portable device which is comprised of (a) a device for holding a disposable package with at least one but preferably a number of drug containers, (b) a mechanical mechanism (e.g. piston or vibrator for moving the contents of a container (on the package) through a porous membrane (c) a device for separately measuring the inspiratory flow rate and inspiratory volume of a patient, and (d) a switch for automatically releasing or firing the mechanical means after the inspiratory flow rate and/or volume reaches a predetermined point. If the device is electronic it also includes (e) a source of power.

The device for holding the disposable package may be nothing more than a narrow opening created between two outwardly extending bars or may include additional components such as one or more wheels, sprockets or rollers notably mounted on the end(s) of such bars. The rollers may be spring mounted so as to provide constant pressure against the surface(s) of the package. The device may also include a transport mechanism which may include providing drive power to roller(s) so that when they are rotated, they move the package from one container to the next. A power source driving the roller(s) can be programmed to rotate the rollers only enough to move the package from one container to the next. In order to use the device, the device must be "loaded," i.e. connected to a package which includes drug dosage units having liquid, flowable formulations of pharmaceutically active drug therein. The entire device is self-contained, light weight (less than 1 kg preferably less than 0.5 kg loaded) and portable.

FIG. 10 shows a cross-sectional view of a hand held, self-contained, portable, breath-actuated inhaler device 50 which can be used in the method of the present invention. The device 50 is shown with a holder 60 having cylindrical side walls and a hand grip 61. The holder 2 is "loaded" in that it includes a package 51. The package 51 includes a plurality of containers 56 connected by a connecting member 65.

The embodiment shown in FIG. 10 is a simple version of a device 50 which may be manually actuated and loaded. More specifically, the spring 62 may be compressed by the user until it is forced down below the actuation mechanism 63. When the user pushes the actuation mechanism 63 the spring 62 is released and the mechanical means in the form of a plate 24 is forced upward against a container 56. When the container 56 is compressed its contents are forced out through the channel 57 and membrane 59 and aerosolized. Another container 56 shown to the left is unused. A top cover sheet 64 has been peeled away from the top of the membrane 59 by a peeling means 25. The embodiment of FIG. 10 could provide the same results as a conventional metered dose inhaler. However, the device of FIG. 10 would not require the use of low boiling point propellants such as low boiling point fluorocarbons. Numerous additional features and advantages of the present invention can be obtained by utilizing the monitoring and electronic components described below.

The device must be capable of aerosolizing drug formulation in a container and preferably does such based on pre-programmed criteria which are readable by the microprocessor 26. The details of the microprocessor 26 and the details of other drug delivery devices which include a microprocessor and pressure transducer of the type used in connection with the present invention are described and disclosed within U.S. patent application Ser. No. 07/664,758 filed on Mar. 5, 1991 entitled "Delivery of Aerosol Medications for Inspiration" which application is incorporated in its entirety herein by reference, and is specifically incorporated in order to describe and disclose the microprocessor and program technology used therewith. The use of such a microprocessor with a drug delivery device is disclosed in our earlier filed U.S. patent application Ser. No. 08/065,660 filed May 21, 1993 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 26, containing read only memory which in turn contains the pre-programmed information, is plugged into the device. For each of these three embodiments, changing the programming of the memory device readable by microprocessor 26 will radically change the behavior of the device by causing microprocessor 26 to be programmed in a different manner. This may be done to accommodate the needs of different patients and/or different insulin formulations with different concentrations.

Microprocessor 26 sends signals via electrical connection 27 to electrical actuation device 28 which actuates the means 63 which fires the mechanical plate 24 forcing drug formulation in a container 56 to be aerosolized so that an amount of aerosolized drug is delivered into the inspiratory flow path 54. The device 28 can be a solenoid, motor, or any device for converting electrical to mechanical energy. Further, microprocessor 26 keeps a record of all drug dosing times and amounts using a read/write non-volatile memory which is in turn readable by an external device. Alternatively, the device records the information onto an electronic or magnetic strip on the package 51. The recorded information can be read later by the care-giver to determine the effectiveness of the treatment. In order to allow for ease of use, it is possible to surround the inspiratory flow path 54 with a mouth piece 52.

The electrical actuation means 28 is in electrical connection with the flow sensor 31 which is capable of measuring a flow rate of about 0 to about 800 liters per minute. It should be noted that inhalation flow rates are less than exhalation rates, e.g. max for inhalation 200 lpm and 800 lpm for exhalation. The flow sensor 31 includes screens 32, 33 and 34 which are positioned approximately ¼" apart from each other.

Tubes 35 and 36 open to the area between the screens 32, 33 and 34 with the tubes 35 and 36 being connected to a conventional differential pressure transducer 37. Another transducer designed to measure outflow through the opening 38 is also preferably included or the flow sensor 31 is designed so that the same components can measure inflow and outflow. When the user draws air through inspiratory flow path 54, air is passed through the screens 32, 33 and 34 and the air flow can be measured by the differential air pressure transducer 37. Alternatively, other means to measure pressure differential related to air flow, such as a conventional measuring device in the air way, may be used. The flow sensor 31 is in connection with the electrical actuation means 28 (via the connector 39 to the processor 26), and when a threshold value of air flow is reached (as determined by the processor 26), the electrical actuation means 28 fires the release of a mechanical means 63 releasing the plate 24 which forces the release of formulation from a container 56 so that a controlled amount of respiratory drug is delivered to the patient. The microprocessor 26 is also connected via connector 40 to an optionally present vibrating device 60 which may be activated.

Vibration Device

The ultrasonic vibrations are preferably at right angles to the plane of the membrane 14 and can be obtained by the use of a piezoelectric ceramic crystal or other suitable vibration device 60. The vibrating device 60 in the form of a piezoelectric crystal may be connected to the porous membrane 59 by means of an attenuator horn or acoustic conduction mechanism, which when correctly matched with the piezoelectric crystal frequency, efficiently transmits ultrasonic oscillations of the piezoelectric crystal to the resonance cavity and the porous polycarbonate membrane and if sized correctly permits the ultrasonic energy to be focused in a polycarbonate membrane 59 allowing for maximum use of the energy towards aerosolizing the liquid formulation 56. The size and shape of the attenuator horn is not of particular importance. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of producing a signal having a frequency of from about 800 kilohertz (Khz) to about 4,000 kilohertz. The power output required depends upon the amount of liquid being nebulized per unit of time and the area and porosity of the polycarbonate membrane used for producing the drug dosage unit and/or the efficiency of the connection.

Vibration is applied while the formulation 56 is being forced from the pores of the polycarbonate membrane 59. The formulation can be aerosolized with only vibration i.e., without applying pressure. Alternatively, when vibration is applied in certain conditions the pressure required for forcing the liquid out can be varied depending on the liquid, the size of the pores and the shape of the pores but is generally in the range of about one to 200 psi, preferably 50 to 125 psi and may be achieved by using a piston, roller, bellows, a blast of forced compressed gas, or other suitable device. The vibration frequency used and the pressure applied can be varied depending on the viscosity of the liquid being forced out and the diameter and length of the openings or pores. In general, the present invention does not create effective aerosols if the viscosity of the liquid is greater than about 50 centipoises.

When small aerosolized particles are forced into the air, the particles encounter substantial frictional resistance. This may cause particles to slow down more quickly than desired and may result in particles colliding into each other and combining, which is undesirable with respect to maintaining the preferred particle size distribution within the aerosol. In order to aid in avoiding the particle collision problem, it is possible to include a means by which air or any other gas is forced through openings as the aerosol is forced out of the porous membrane. Accordingly, an air flow is created toward the patient and away from the nozzle opening which carries the formed particles along and aids in preventing their collision with each other. The amount of gas forced from the openings will vary depending upon the amount of aerosol being formed. However, the amount of gas is generally five to two hundred times the volume of the liquid formulation within the container. Further, the flow velocity of the gas is generally about equal to the flow velocity of the aerosolized particles being forced from the nozzle. The shape of the container opening, the shape of the membrane covering that opening, as well as the positioning and angling of the gas flow and particle flow can be designed to aid in preventing particle collision. When the two flow paths are substantially parallel, it is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangle. Using such a configuration makes it possible to better utilize the air flow relative to all of the particles being forced form the container. When a circular opening is used, particles which are towards the center of the circle may not be carried along by the air being forced from the openings and will collide with each other. The elongate rectangle could be formed in a circle, thereby providing an annular opening and air could be forced outward from the outer and inner edges of the circle formed. Further details regarding such are described in U.S. patent application Ser. No. 08/247,012 filed May 20, 1994 which is incorporated herein by reference to disclose and describe such.

Safety Features

The methodology and devices of the present invention can prevent misuse by others such as children. The device shown within FIG. 2 is designed to be reusable. More specifically, the drug delivery device can be "loaded" with a cassette of the type shown within either of FIGS. 3 and 4. The cassette is comprised of an outer cover 30, a canister 3 and top nozzle piece 31. The components are shown in a disassembled state in FIG. 3. A different embodiment of such components are shown in an assembled state within FIG. 4.

Figures 3, 4:
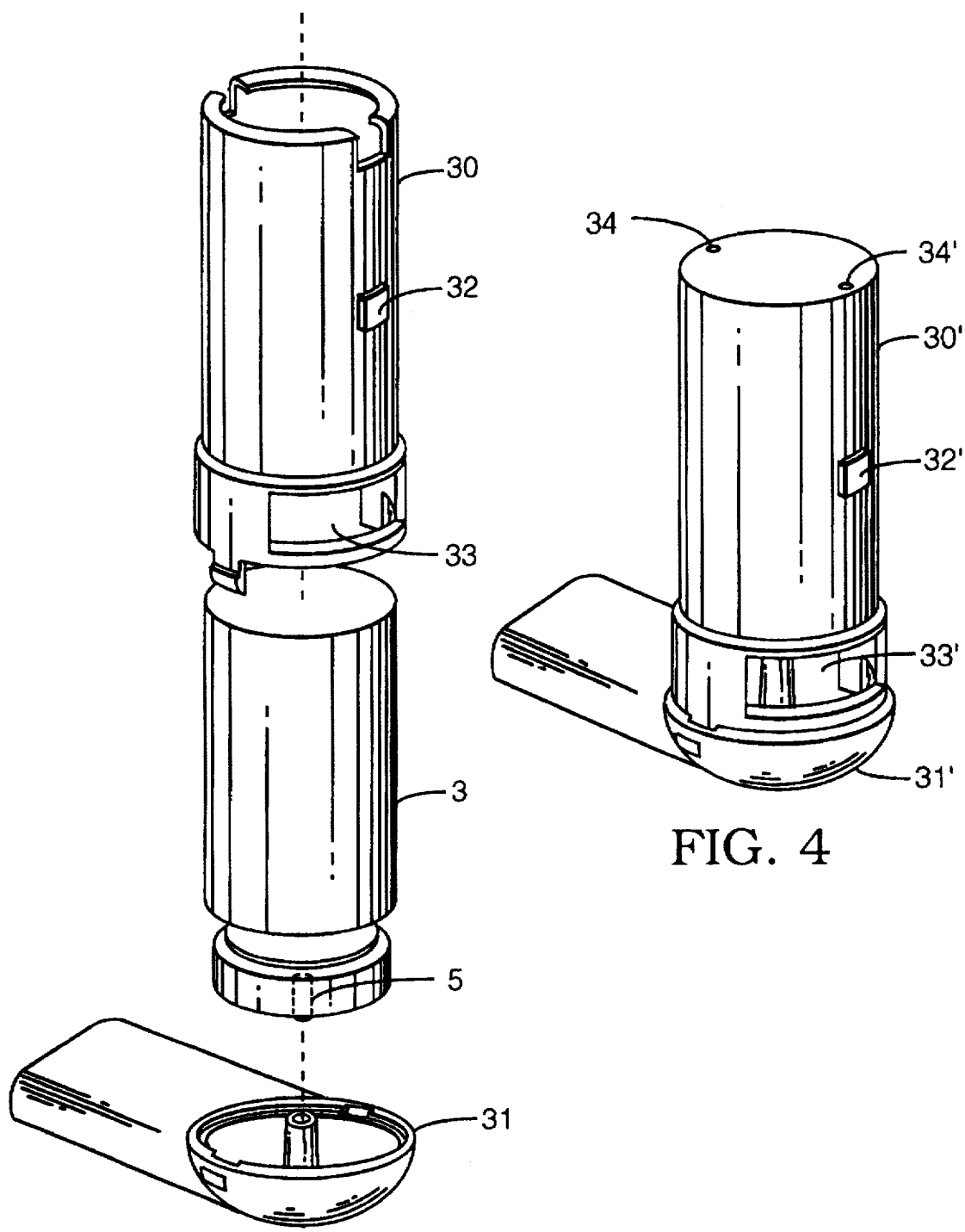
FIG. 3 is a prospective view showing another embodiment of an aerosolized drug delivered.
FIG. 4 is a cross-sectional view of an insulin-containing package of the invention.

In essence, the cassette shown in FIG. 3 is somewhat less secure than the cassette shown within FIG. 4. As indicated, the top portion of the cover 30 is open within FIG. 3. This allows one to force the canister 3 downward and open the valve 5 to allow release of drug. However, in the embodiment shown in FIG. 4, there is no general opening but only two small openings 34 and 34'. Using the embodiment shown in FIG. 3, the cassette is loaded within the device shown in FIG. 2 and a motor driven piston forces the bottom of the canister 3 downward actuating the valve 5 to an open position. In accordance with the embodiment shown within FIG. 4, a two-pronged fork device is positioned over the end portion of the cover 30'. Each prong of the fork protrudes through an opening 34 and 34' allowing the canister 3 to be forced downward so that the valve 5 can be opened. It should be pointed out that when the cover 30 is attached to the top nozzle piece 31, they can be sealed together using a fast-acting glue or any appropriate means making it impossible to separate the components.

Insulin Containing Package

A package 51 which includes containers 56 is shown within the FIG. 10. This type of package includes the insulin formulation in a flowable form within the container 56.' However, in another embodiment the insulin is maintained in a dry state substantially free of water in one container while the liquid component of the formulation such as the water is maintained in a separate container. Such a package is shown in FIG. 11.

Figure 11:
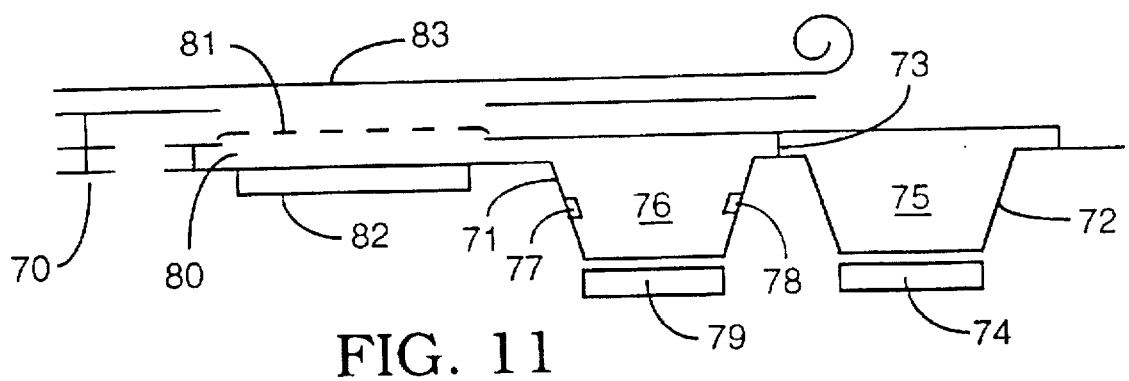
FIG. 11 is a schematic view of an insulin formulation package.

The package 70 of a FIG. 11 includes a first container 71 and a second container 72. The containers 71 and 72 are in fluid connection with each other but the fluid connection is interrupted by a membrane 73 which membrane can be ruptured by the application of pressure in an amount of about 50 psi or less. A device such as the component 74 forces against the bottom of the container 72 and forces the contents 75 (which is liquid) against the membrane 73 which is then ruptured. The liquid 75 then enters the container 71 and mixes with the dry powder 76 present with the container 71. The container 71 may include mixing components 77 and 78. These components may be vibrating devices, ultrasonic devices or other suitable mechanisms allowing for the mixing of the liquid with the dry insulin. When the mixing is completed the component 79 is forced against the container 71 forcing the insulin formulation present therein into the chamber 80. Once the formulation is in the chamber 80 it is there under pressure and can be moved through the membrane 81 by the application of that pressure and/or by the use of a vibrating device 82. The formulation is moved through the membrane 81 only after removal of the cover sheet 83.

Packages such as shown within the FIG. 11 are described within U.S. patent application Ser. No. 08/247,012 filed May 20, 1994 which application is incorporated herein by reference to disclose and describe such packages. The Membrane 81 includes pores having a diameter in the range of about 0.25 micron to about 6 microns and a pore density in the range of $1 \times 10^4$ to about $1 \times 10^8$ pores per square centimeter. The porous membrane 81 is preferably comprised of a material having a density in the range of about 0.25 to 3.0 mg/cm$^2$, more preferably about 1.7 mg/cm$^2$ and a thickness of about 2 to about 20 microns, more preferably 8 to 12 microns. The liquid 75 present in the container 72 is preferably capable of dissolving the insulin. The insulin powder 76 is preferably completely dissolved within the container 71 prior to being forced into the chamber 80. Dissolving the insulin makes it easier to move the insulin through the pores of the membrane 81 and create a fine mist aerosol. Keeping the dried insulin apart from the liquid makes it possible to maintain a longer shelf life.

Dynamic Particle Size Control

Devices for delivering aerosolized insulin and in particular the aqueous system device will generally operate consistently. However, as the aerosolized particles are released, the size of the particles can decrease due to evaporation of water. The rate of decrease can be effected by the surrounding atmosphere. Further, in particularly humid atmospheres, the particles can be caused to grow in size. In order to provide for greater consistency it is possible to add energy such as heat to the atmosphere surrounding the released aerosolized particles. This is done by an appropriate means such a heating coil or other means which can add energy to the atmosphere and thereby minimize the effect, if any, of humidity in the surrounding atmosphere in terms of effecting particle size. It is also possible to add water vapor to the surrounding particles so as to saturate the environment and thereby provide for a consistent particle size which is delivered to the patients. Further details regarding means for adjusting particle size are disclosed within U.S. patent application Ser. No. 08/313,461 entitled "Dynamic Particle Size Reduction for Aerosolized Drug Delivery", filed on Sep. 27, 1994, which application is incorporated herein by reference in its entirety and specifically incorporated to disclose and describe means for dynamically adjusting the size of aerosolized particles.

The instant invention is shown and described herein in which is considered to be the most practical and preferred embodiments. It is recognized, however, that the departures may be made therefrom which are within the scope of the invention and that obvious modifications will occur to one skilled in the art upon reading this disclosure.

We claim:

1. A method of administering insulin to a human patient, comprising:

determining a drug release point based on real time values of both a patient's inspiratory flow rate and inspiratory volume;

releasing an aerosolized formulation of insulin into the patient's inspiratory flow path when the inspiratory flow rate is in the range of from about 0.10 to 2.0 liters/second and the patient's inspiratory volume is in the range of from about 0.15 to about 0.80 liters.

2. The method of claim 1, wherein the inspiratory flow rate is in the range of from about 0.2 to about 1.8 liters/second and the inspiratory volume is in the range of from about 0.15 to about 0.40 liters.

3. The method of claim 1, wherein the inspiratory flow rate is in the range of from about 0.15 to about 1.8 liters/second and the inspiratory volume is in the range of from about 0.15 to about 0.25 liters, and wherein the insulin formulation is released at a velocity such that particles of insulin formulation are at zero velocity or reduce to zero velocity after traveling 2 cm or less from a point of release in the absence of the patient's inspiration, and wherein the aerosolized insulin formulation has a particle size in the range of from about 0.5 to 12 microns.

4. The method of claim 1, wherein the determining and releasing are carried out during a single inhalation of the patient.

5. The method of claim 1 wherein the aerosolized insulin formulation is in the form of aerosolized particles of a solution.

6. The method of claim 5, wherein the solution is an aqueous solution.

7. The method of claim 1, wherein the aerosolized insulin formulation is in the form of aerosolized particles of a dry insulin powder.

8. The method of claim 1, wherein the determining is carried out by measuring via electronic air flow measurement components.

9. The method of claim 1, wherein the determining is carried out by measuring via mechanical air flow measurement components.

10. The method of claim 1, wherein the releasing is begun and completed while the inspiratory flow rate is in the range of from about 0.10 to about 2.0 liters/second and wherein the releasing is begun while the inspiratory volume is in the range of about 0.15 to about 0.40 liters.

11. The method of claim 1, further comprising:

repeating the determining and releasing a plurality of times.

12. The method of claim 1, further comprising:

monitoring serum glucose levels in the patient; and repeating the determining, releasing and monitoring a plurality of times over a period of time so as to maintain a desired serum glucose level in the patient.

13. The method as claimed in claim 12, wherein the amount of insulin administered and the glucose level monitored are continually recorded and adjustments are made in the amount of insulin administered based on the effect of insulin administration on the glucose levels of the patient.

14. The method as claimed in claim 12, wherein the amount of insulin administered is in the range of 1 unit per day to 50 units per day and wherein the desired serum glucose level in the patient is within the range of 50 mg/dl to 300 mg/dl.

15. The method of claim 11, further comprising:

orally administering a sulfonylurea drug to the patient.

16. The method of claim 15, wherein the sulfonylurea drug is selected from the group consisting of acetohexamide, chlorpropamide, tolazamide, tolbutamide, glipzide and glyburide.

17. A method of treating diabetes mellitus, comprising:

repeatedly administering to a patient a predetermined amount of aerosolized insulin formulation wherein the aerosolized insulin formulation is administered at substantially the same inspiratory flow rate and inspiratory volume so as to repeatedly administer substantially the same amount of insulin formulation to patient at each administration.

18. The method of claim 17, wherein the insulin formulation is repeatedly administered at an inspiratory flow rate in the range of about 0.10 to about 2.0 liters/second and an inspiratory volume in the range of about 0.15 to about 0.80 liters.

19. The method of claim 17, wherein the inspiratory flow rate and inspiratory volume are within ±10% at each repeated administration of insulin formulation.

20. A disposable insulin formulation package, comprising:

a first container having therein dry insulin the container comprising at least one wall which is collapsible by the application of a force causing a pressure of about 20 psi to 100 psi and further comprising a porous membrane with pores having a diameter of about 0.25 micron to about 6 microns; and a second container having a flowable liquid therein connected to and in fluid connection with the first container, the fluid connection being interrupted by a membrane which is ruptured by the application of pressure of about 50 psi or less.

* * * * *